United States Patent
Chen et al.

(10) Patent No.: US 12,391,986 B2
(45) Date of Patent: Aug. 19, 2025

(54) ANTI-COUNTERFEIT TAGS USING BASE RATIOS OF POLYNUCLEOTIDES

(71) Applicant: MICROSOFT TECHNOLOGY LICENSING, LLC, Redmond, WA (US)

(72) Inventors: Yuan-Jyue Chen, Seattle, WA (US); Karin Strauss, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 570 days.

(21) Appl. No.: 17/490,694

(22) Filed: Sep. 30, 2021

(65) Prior Publication Data
US 2023/0101083 A1    Mar. 30, 2023

(51) Int. Cl.
*G16B 50/40*      (2019.01)
*C12N 15/10*      (2006.01)
*C12Q 1/6869*      (2018.01)

(52) U.S. Cl.
CPC ....... *C12Q 1/6869* (2013.01); *C12N 15/1065* (2013.01); *G16B 50/40* (2019.02)

(58) Field of Classification Search
CPC .. C12Q 1/6869; C12Q 1/6876; C12Q 1/6816; C12N 15/1065; G16B 50/40
See application file for complete search history.

(56) References Cited

U.S. PATENT DOCUMENTS

| | | | |
|---|---|---|---|
| 8,415,164 B2 | 4/2013 | Hayward et al. | |
| 2006/0121181 A1 | 6/2006 | Sleat | |
| 2006/0286569 A1 | 12/2006 | Bar-Or et al. | |
| 2007/0048761 A1 | 3/2007 | Reep | |
| 2008/0293052 A1 | 11/2008 | Liang | |
| 2008/0299559 A1 | 12/2008 | Kwok | |
| 2009/0163366 A1 | 6/2009 | Nickerson | |
| 2011/0165569 A1 | 7/2011 | Macula | |
| 2012/0135413 A1 | 5/2012 | Brown et al. | |
| 2013/0271758 A1 | 10/2013 | Marchant | |
| 2015/0018538 A1 | 1/2015 | Berrada et al. | |
| 2015/0104802 A1 | 4/2015 | Reep | |
| 2015/0141264 A1 | 5/2015 | Jung | |
| 2015/0183257 A1 | 7/2015 | Glendenning | |
| 2015/0379903 A1 | 12/2015 | McLeod | |
| 2016/0115544 A1 | 4/2016 | Elzinga | |
| 2017/0021611 A1 | 1/2017 | Jung et al. | |
| 2018/0114168 A1 | 4/2018 | Ryan | |
| 2019/0241982 A1 | 8/2019 | Hogan | |
| 2019/0271032 A1 | 9/2019 | Owen | |
| 2019/0338354 A1 | 11/2019 | Gonzales, Jr. | |
| 2020/0074124 A1 | 3/2020 | Zografos | |
| 2020/0074478 A1 | 3/2020 | Peters | |
| 2020/0098460 A1 | 3/2020 | Banks et al. | |
| 2020/0370111 A1 | 11/2020 | Ceze et al. | |
| 2020/0385824 A1 | 12/2020 | Hogan | |
| 2021/0019973 A1 | 1/2021 | Yin | |
| 2021/0108192 A1 | 4/2021 | Mattei | |
| 2021/0108194 A1 | 4/2021 | Roquet et al. | |
| 2021/0142868 A1* | 5/2021 | Copin | C12Q 1/6869 |
| 2021/0277461 A1* | 9/2021 | Glezer | C12Q 1/6869 |
| 2023/0002837 A1 | 1/2023 | Borg et al. | |
| 2023/0054038 A1 | 2/2023 | Bhuyan et al. | |
| 2023/0101409 A1 | 3/2023 | Chen et al. | |
| 2023/0125457 A1 | 4/2023 | Chen et al. | |
| 2024/0093317 A1 | 3/2024 | Karlikow | |
| 2024/0257147 A1 | 8/2024 | Owen | |

FOREIGN PATENT DOCUMENTS

| | | | | |
|---|---|---|---|---|
| EP | 1237327 A2 | 9/2002 | | |
| ES | 2273531 A1 | 5/2007 | | |
| KR | 20200108149 A * | 9/2020 | | C12Q 1/68 |
| WO | 2004063856 A2 | 7/2004 | | |
| WO | WO-2012094492 A2 * | 7/2012 | | C12N 15/1065 |
| WO | 2016114808 A1 | 7/2016 | | |

(Continued)

OTHER PUBLICATIONS

Hughes et al., "Synthetic DNA Synthesis and Assembly: Putting the Synthetic in Synthetic Biology," 2017. Cold Spring Harbor Laboratory Press. pp. 1-17. doi: 10.1101/cshperspect.a023812 (Year: 2017).*

Palluk et al., "De novo DNA synthesis using polymerasenucleotide conjugates," 2018. Nature Biotechnology. vol. 36. pp. 645-650 and Online Methods. (Year: 2018).*

Anavy et al., "Data storage in DNA with fewer synthesis cycles using composite DNA letters," 2019. Nature Biotechnology. vol. 37, pp. 1229-1236. (Year: 2019).*

Machine translation of KR20200108149A. Obtained Sep. 27, 2023. (Year: 2020).*

Muhire et al., "SDT: A Virus Classification Tool Based on Pairwise Sequence Alignment and Identity Calculation, " PLoS One, vol. 9, Issue 9, e10827. (Year: 2014).*

Machine Translation of WO-2020218489-A1. (Year: 2020).*

(Continued)

*Primary Examiner* — Gary Benzion
*Assistant Examiner* — Francesca Filippa Giammona
(74) *Attorney, Agent, or Firm* — Benjamin Keim; Newport IP, LLC

(57) ABSTRACT

Multiple polynucleotides with random sequences are collectively used as a molecular anti-counterfeiting tag. The polynucleotides are placed on an item as a molecular identifier of authenticity. Each position within the random sequences is synthesized using a predetermined ratio of nucleoside bases. With this technique the sequence of each polynucleotide is random but the ratio of nucleoside bases over the collection of synthetic polynucleotides is not. Verification of authenticity is achieved by sequencing a portion of the polynucleotides collected from the item and calculating the ratio of nucleoside bases at each position. If these ratios are the same or similar to the ratios used for synthesizing the polynucleotides, then the item is identified as authentic. The ratios of nucleoside bases and a description of the item may be stored in an electronic record that is used for validating authenticity of the item.

17 Claims, 6 Drawing Sheets

(56) References Cited

FOREIGN PATENT DOCUMENTS

| WO | WO-2019152862 A1 * | 8/2019 | ............... C12Q 1/68 |
| WO | WO-2019183359 A1 * | 9/2019 | ........... C12Q 1/6813 |
| WO | 2020028955 A1 | 2/2020 | |
| WO | WO-2020218489 A1 * | 10/2020 | ........... C12Q 1/6886 |
| WO | 2021102579 A1 | 6/2021 | |

OTHER PUBLICATIONS

Wheeler et al., "BLAST QuickStart," Comparative Genomics: vols. 1 and 2. Humana Press. (Year: 2007).*

Palluk, et al., "De Novo DNA Synthesis Using Polymerase-Nucleotide Conjugates", In Journal of Nature Biotechnology, vol. 36, Issue 7, Jun. 18, 2018, pp. 645-650.

"International Search Report and Written Opinion Issued in PCT Application No. PCT/US22/042280", Mailed Date: Jan. 5, 2023, 13 Pages.

"International Search Report and Written Opinion Issued in PCT Application No. PCT/US22/042572", Mailed Date: Dec. 15, 2022, 11 Pages.

"International Search Report and Written Opinion Issued in PCT Application No. PCT/US22/044650", Mailed Date: Dec. 21, 2022, 18 Pages.

Tang, et al., "Enzymatic Polymerization of High Molecular Weight DNA Amphiphiles That Self-Assemble into Star-Like Micelles", In Journal of Advanced Materials, vol. 26, vol. 19, May 21, 2014, pp. 3050-3054.

"Tagsmart", Retrieved from: https://web.archive.org/web/20210530160413/https://tagsmart.com/, Jun. 25, 2021, 2 Pages.

Berk, et al., "Rapid Visual Authentication Based on DNA Strand Displacement", In Journal of ACS Applied Materials & Interfaces, vol. 13, Issue 16, Apr. 14, 2021, pp. 19476-19486.

Doroschak, et al., "Rapid and Robust Assembly and Decoding of Molecular Tags with DNA-based Nanopore Signatures", In Journal of Nature Communications, vol. 11, Issue 1, Nov. 3, 2020, 8 Pages.

Puddu, et al., "Magnetically Recoverable, Thermostable, Hydrophobic DNA/Silica Encapsulates and Their Application as Invisible Oil Tags", In Journal of ACS Nano, vol. 8, Issue 3, Feb. 25, 2014, pp. 2677-2685.

Non- Final Office Action mailed on May 9, 2025, in U.S. Appl. No. 17/511,454, 14 pages.

\* cited by examiner

ANTI-COUNTERFEIT TAGS USING BASE RATIOS OF POLYNUCLEOTIDES

BIOLOGICAL SEQUENCES

Although this application references nucleotide sequences and uses single-letter abbreviations to represent individual nucleic acid bases, it does not include any nucleotide sequences as defined in 37 C.F.R. 1.821 because there are no sequences of ten or more nucleotides.

BACKGROUND

Forgeries and counterfeits are problems in many industries and for many types of valuable items such as artwork, jewelry, wine, foods, and designer brands. Identifying a forgery or counterfeit item can be challenging because a typical purchaser may not be able to distinguish a fake item from an authentic item. One solution is to use anti-counterfeit tags as a marker to identify authentic items. Absence of an anti-counterfeit tag or an incorrect tag may indicate an inauthentic item. Holographic stickers, radio-frequency identification (RFID) tags, and quick response (QR) codes are all used as anti-counterfeit tags.

However, many types of anti-counterfeit tags can themselves be forged by sophisticated bad actors. In response, more complex and sophisticated tags are created. However, increased tag creation costs may discourage producers from labeling their items. Additionally, high cost involved with reading a tag may discourage purchasers from using the tags. Thus, for many items there needs to be a balance between the robustness of a tag and the costs associated with its use. Accordingly, it is desirable to develop new types of anti-counterfeit tags that are relatively inexpensive to produce and validate but expensive to copy or forge. The following disclosure is made with respect to these and other considerations.

SUMMARY

This disclosure provides techniques for creating and using polynucleotides as anti-counterfeit tags. Instead of using a single polynucleotide as a tag, a large number such as millions, billions, hundreds of billions, trillions, or more polynucleotides each with a unique, random sequence of bases are used to tag an item. Each of the polynucleotides is synthesized by a process that creates a random sequence of bases. The synthesis technique uses a specific, predetermined ratio of nucleoside bases for each position when synthesizing a batch of polynucleotides. Synthesis may be performed by any technique for de novo polynucleotide synthesis such as phosphoramidite synthesis or enzymatic synthesis in which a predetermined, specific ratio of nucleotides is provided for each round of polynucleotide extension. Column synthesis is one technique and can create as many as $10^{24}$ polynucleotides with unique, random sequences in a single synthesis run.

It is possible to synthesize many polynucleotide strands each with different random sequences (or "random-mers") in a single batch. However, re-creating the same sequences with specific base-by-base synthesis would require multiple separate synthesis operations and is much more expensive. The techniques of this disclosure take advantage of this cost difference to create anti-counterfeit tags that are much less expensive to generate than to copy or forge.

Each polynucleotide has a random sequence, but when aligned and analyzed as a batch the specific, predetermined ratios of nucleoside bases across all of the synthetic polynucleotides are maintained. For example, a first position in the polynucleotides can be synthesized with 50% adenosine (A) and 50% guanine (G) and a second position in the polynucleotides may be synthesized with 50% thymidine and 50% cytosine (C). This contrasts with a typical synthesis of polynucleotides with random sequences (or "random-mers") that uses an equal ratio of nucleoside bases so that when analyzed as a group each position will have about 25% of each base.

The synthetic polynucleotides may also include alignment regions that are not random and may be used to align the random portions of the polynucleotide. The alignment regions share the same position (e.g., at the 5' end, the 3' end, or within the random sequences) in all of the synthetic polynucleotide sequences. The alignment regions may, but do not necessarily, have the same sequence for all of the synthetic polynucleotides. In some implementations, the alignment regions are primer binding sites. Alignment enables identification of specific positions in the collection of polynucleotides and calculation of position-specific ratios of nucleoside bases.

The ratio of nucleoside bases at a specific position in the collection of random polynucleotides may be mapped to a "composite letter" that can represent, for example, a binary value. For example, bits 00 can be represented as a composite letter which is encoded by synthesizing polynucleotides with 50% A and 50% T mixture of nucleoside bases. There may be other composite letters that form an alphabet such as, for example, 50% G and 50% C representing bits 01, 50% A and 50% G representing bits 10, and 50% T and 50% C representing bits 11. The composite letters provide mappings between one of multiple discrete sets of polynucleoside base ratios and another arbitrary value such as binary digits.

Once synthesized, and prior to application to an item, the polynucleotides may be sequenced. If sequenced, the sequences can be stored in an electronic record. Whether the synthetic polynucleotides are sequenced or not, the ratios of nucleoside bases at each position in the sequences are stored in the electronic record. If composite letters are used, the composite letters encoded by the synthetic polynucleotides may also be stored in the electronic record such as, for example, as a binary number. The electronic record associates the predetermined ratios of nucleoside bases with a description of the tagged item such as a picture or textual description. The electronic record may be maintained by a trusted third party and serves as an objective source for validating the authenticity of the tagged item. The electronic record may be maintained on a network-accessible system such as a cloud database. The contents of the electronic record may be encrypted, converted to a hash, or otherwise protected from unauthorized access.

Authenticity of the item is determined by collecting polynucleotides from the item and sequencing a portion of the polynucleotides to obtain retrieved sequences. Sequencing may be performed by any sequencing technology such as, but not limited to, nanopore sequencing. The retrieved sequences may be provided to a computing device connected to the electronic record. The retrieved sequences are aligned to create an alignment of the retrieved sequences. If present, the alignment regions may be used to assist in making the alignment. Ratios of nucleoside bases at each position in the alignment of retrieved sequences are calculated. The calculated base ratios from the alignment of the retrieved sequences are compared to the predetermined ratios of nucleoside bases stored in the electronic record.

If there is a match between the calculated base ratios and the predetermined ratios of nucleoside bases stored in the electronic record, an indication of authenticity is returned. The match need not be a perfect match. For example, the ratios of nucleoside bases may be considered equivalent if they are within a threshold amount of each other (e.g., 48% A and 52% T may be considered the same as 50% A and 50% T) and/or if ratios match at least a threshold portion of the sequences (e.g., the same ratios along 80% or more of the length of the sequences).

Because the ratios of nucleoside bases are used to determine authenticity rather than the specific sequences of the synthetic nucleotides, it is possible to validate the authenticity of an item without necessarily sequencing all of the polynucleotides collected from the item. This reduces the sequencing cost and accordingly the cost to read the anti-counterfeit tag. Any sized portion of the synthetic polynucleotides may be sequenced and used for the comparison so long as it is representative of the total set of polynucleotides. For example, the portion of polynucleotides that are sequenced may be 10% or less of the total number of polynucleotides collected from the item.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. The figures are schematic representations and items shown in the figures are not necessarily to scale.

DETAILED DESCRIPTION

Nucleic acids have been previously used as anti-counterfeit tags as described in U.S. Pat. No. 5,451,505. However, the '505 patent and other previous work discussing polynucleotide tags use the sequence of one or a few polynucleotides as the tag. Due to advances in polynucleotide synthesis and sequencing technology, simple polynucleotide tags can now be readily copied by a bad actor if the sequence is known.

One technique to make it more difficult for the bad actor hides the actual polynucleotide tag by mixing it with many other polynucleotides. The actual tag molecule has unique primer binding sites and can be selectively amplified by polymerase chain reaction (PCR) and sequenced to confirm the authenticity of an item. To forge this type of tag the bad actor would need to sequence and synthesize all the polynucleotides because the specific sequence used as the tag is not known to the bad actor. However, knowledge of the primers for amplifying the actual polynucleotide tag is needed to check the tag. If the primers are available to a purchaser or potential purchaser so that they can independently determine the authenticity of the item, a bad actor can also learn the primer sequences. Once the primers and the sequence of the actual polynucleotide tag are known, it is relatively easy for a bad actor to synthesize many copies of that sequence and create fake anti-counterfeit tags.

The techniques of this disclosure use a large number of polynucleotides (e.g., $10^{10}$ $10^{12}$, $10^{18}$, $10^{24}$) instead of just one or a few polynucleotides to create the anti-counterfeit tag. The synthetic polynucleotides are created with random sequences which can be synthesized inexpensively in large numbers. Examples of some techniques that use large numbers of polynucleotides with random sequences as anti-counterfeit tags are discussed in U.S. Pat. Application No. entitled "Anti-Counterfeit Tags Using High-Complexity Polynucleotides" filed on the same day as this application.

Anti-counterfeit tags that use a large number of random polynucleotides collectively as the tag are difficult to forge. Yet verification costs can be high due to the expense of sequencing a large number of polynucleotides. Using the ratio of nucleoside bases at each position in the synthetic polynucleotides rather than the full sequences provides an anti-counterfeit tag that is expensive to forge yet is less expensive to sequence and verify.

Detail of procedures and techniques not explicitly described or other processes disclosed of this application are understood to be performed using conventional molecular biology techniques and knowledge readily available to one of ordinary skill in the art. Specific procedures and techniques may be found in reference manuals such as, for example, Michael R. Green & Joseph Sambrook, *Molecular Cloning: A Laboratory Manual*, Cold Spring Harbor Laboratory Press, $4^{th}$ ed. (2012).

Figure 1:
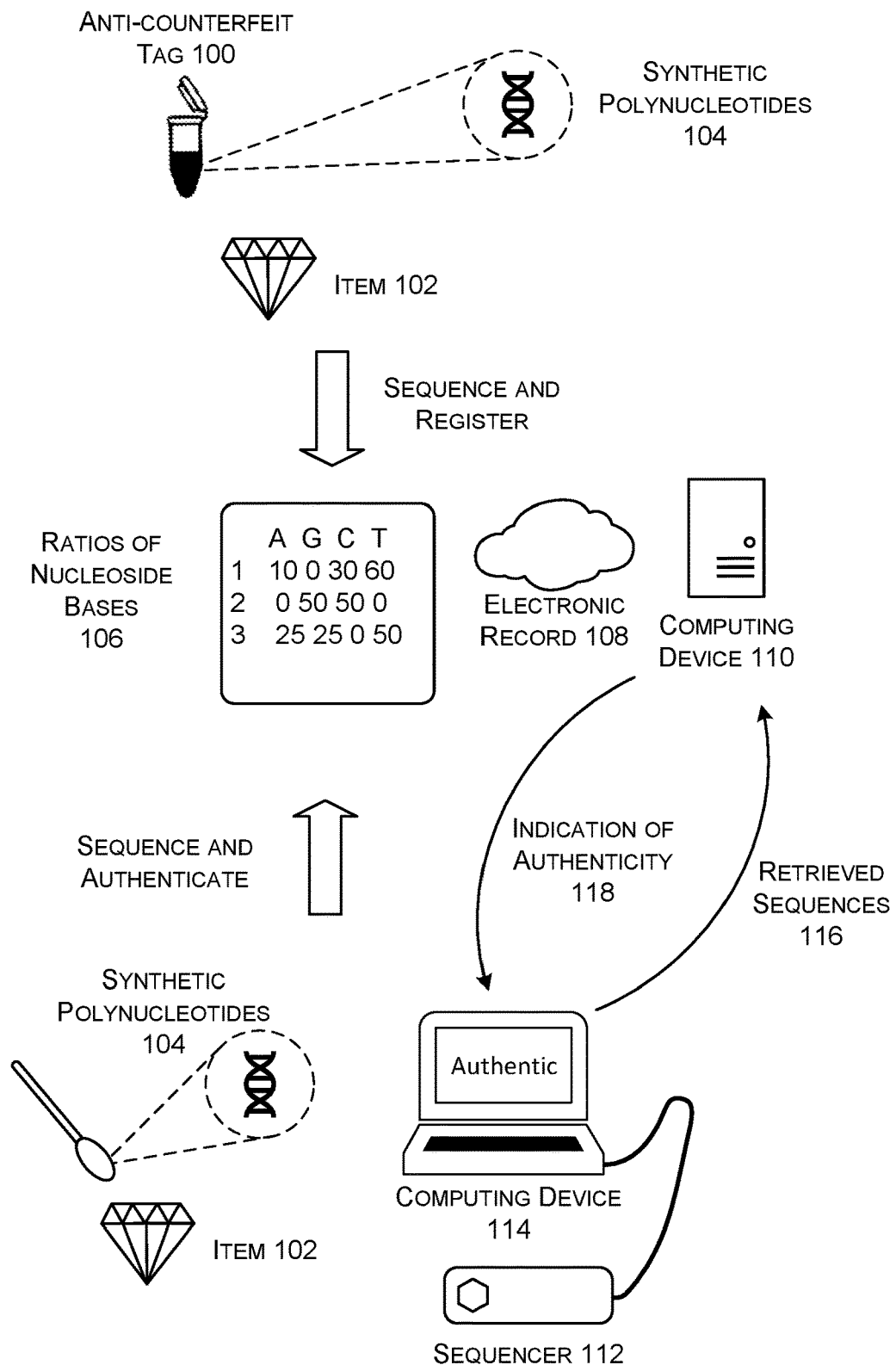
FIG. 1 illustrates use of synthetic polynucleotides with random sequences and an electronic record to validate the authenticity of an item.

FIG. 1 shows the use of an anti-counterfeit tag 100 to label and identify an item 102. The anti-counterfeit tag 100 contains multiple synthetic polynucleotides 104 with random sequences with a specific, predetermined ratio of nucleotides at each position in the random sequences. The plurality of polynucleotides 104 and the ratios of nucleoside bases rather than any single polynucleotide sequence functions as the anti-counterfeit tag 100. Thus, forging the anti-counterfeit tag 100 requires synthesizing a batch of polynucleotides that have the same ratios of nucleoside bases at each position as the synthetic polynucleotides.

Polynucleotides include both deoxyribonucleic acid (DNA), ribonucleic acid (RNA), and hybrids containing mixtures of DNA and RNA. DNA and RNA include nucleotides with one of the four natural bases cytosine (C), guanine (G), adenine (A), thymine (T), or uracil (U) as well as unnatural bases, noncanonical bases, and modified bases. The synthetic polynucleotides 104 may be double-stranded polynucleotides such as in one implementation double-stranded DNA. The synthetic polynucleotides 104 have non-natural sequences that are not derived from natural or biological sources.

Techniques known to those of ordinary skill in the art for synthesizing polynucleotides with random sequences may be adapted to create polynucleotides that have a specific, predetermined ratio of nucleoside bases at each position. Techniques for synthesis of polynucleotides with random sequences are discussed in Meiser, Koch, J., Antkowiak, P. L. et at. DNA synthesis for true random number generation. *Nat Commun* 11, 5869 (2020). The enzyme terminal deoxynucleotidyl transferase (TDT) used in enzymatic polynucleotide synthesis is known to generate random sequences when provided with a mixture of nucleoside bases. See Fowler J D, Suo Z (2006) *Biochemical, Structural, and Physiological Characterization of Terminal Deoxynucleotidyl Transferase*. Chemical Reviews 106(6):2092-2110.

Conventional random-mer synthesis techniques may be adapted to create a population of polynucleotides that, as a population, has specific ratios of nucleoside bases at each position. In these techniques, the base added to any given strand at any round of synthesis is determined stochastically leading to synthesis of polynucleotides with random sequences. The probability of a given base being incorporated is determined by its relative concentration to other bases. If only a single nucleoside base is provided, 100% of the polynucleotides will have that base. If each nucleoside base (e.g., A, G, C, and T) is provided in equal quantity, each nucleoside base has an equal probability of being incorporated the polynucleotides creating a population of polynucleotides that has an equal ratio (i.e., 25% of each) of the nucleoside bases.

Many other ratios are also possible. For example, during one round of polynucleotide extension, a mixture of 20% A, 45% C, 10% G, and 25% T may be provided. This will create a population of polynucleotides in which 25% of the strands have an A, 45% have a C, 10% have a G, and 25% have a T have at that position. This may be represented as (20, 45, 10, 25) where the values represent the percent chance of incorporation of A, C, G, and T, respectively.

The specific ratios of nucleoside bases at each position in the synthetic polynucleotides are determined in advance. The specific ratios of nucleoside bases are implemented by providing a mixture of nucleoside phosphoramidites in the case of phosphoramidite synthesis or nucleoside triphosphate in the case of enzymatic synthesis with the specified ratio of bases during a round of synthesis. Nucleotides with different bases may be incorporated at different rates during polynucleotide synthesis. Stated differently, the enzymes or chemical reactions used to synthesize polynucleotide chains may preferentially incorporate some nucleoside bases at a higher rate than others. See Motea E A and Berdis A J. Terminal deoxynucleotidyl transferase: the story of a misguided DNA polymerase. *Biochim Biophys Acta.* 2010; 1804(5):1151-1166. The degree to which one type of nucleotide is preferentially incorporated over the others may be determined experimentally. The ratio of nucleotides provided to the system is adjusted accordingly so that the polynucleotide strands generated will have the intended ratio of nucleoside bases at each position. Thus, the ratio of nucleotides provided to a synthesis system may be slightly different than the ratio of incorporated bases.

Synthesis may initially create single-stranded polynucleotides with random sequences that have the specific, predetermined ratios of nucleoside bases. If double-stranded polynucleotides are used for the anti-counterfeit tag 100, strands complementary to the synthesized polynucleotides may be created by polymerase chain reaction (PCR) to form double-stranded molecules.

The anti-counterfeit tag 100 may contain a large number of synthetic polynucleotides 104 such as from about $10^2$ to about $10^{24}$ different polynucleotides or more. For example, an anti-counterfeit tag 100 may contain about $10^{12}$, $10^{18}$, or $10^{24}$ polynucleotide strands each with different, random sequences. Due to the random order of nucleoside bases joined to create the polynucleotides, each of the synthetic polynucleotides 104 will likely have a unique sequence different from all the others. There is a very small possibility that two or more of the synthetic polynucleotides 104 will have the same sequence. However, for practical purposes, it can be assumed that all the polynucleotides synthesized in one batch and used as an anti-counterfeit tag 100 have different sequences.

The synthetic polynucleotides 104 are placed on an item 102. The item 102 may be a high-value item such as a work of art, a jewel, a banknote, a document, an antique, etc. The synthetic polynucleotides 104 may be placed directly on the surface of the item 102 for example in liquid or power form. If the item 102 itself is liquid, the synthetic polynucleotides 104 may be mixed into the item 102. The synthetic polynucleotides 104 may be applied "naked" without any modification or they may be protected with stabilizing agents or encapsulated by a protective coating. Multiple techniques for stably storing polynucleotides have been developed for storing biological samples and are known to those of ordinary skill in the art. Any suitable technique may be adapted for use with the item 102 depending on the composition of the item 102. In some implementations, the synthetic polynucleotides 104 may be placed on, under, or in a second taggant that is visibly detectable such as a QR code, RFID tag, or holographic sticker.

Because the synthetic polynucleotides 104 are synthesized by a process that creates random sequences, the sequences of the synthetic polynucleotides 104 are not known in advance of synthesis. The ratios of nucleoside bases 106 at each position in the random sequences are known for the entire population of synthetic polynucleotides 104 but the sequence any the individual polynucleotides are not known. Following synthesis, and before application to the item 102, the synthetic polynucleotides 104 may be sequenced. Some techniques for synthesizing multiple polynucleotides with random sequences create only one copy of each sequence. And most sequencing procedures discard the polynucleotide strands following sequencing. Accordingly, to both sequence a synthetic polynucleotide 104 with a random sequence and to also place a polynucleotide strand with the same sequence on an item 102 as an anti-counterfeit tag 100 there may need to be multiple copies of each polynucleotide strand.

The synthesized polynucleotide strands may be copied to generate multiple copies. Copying may be performed even if the synthetic polynucleotides 104 are not sequenced. Any technique that creates multiple copies of an existing polynucleotide strand may be used. Current techniques known to those of ordinary skill in the art for making multiple copies of existing polynucleotide strands include enzymatic methods. One enzymatic technique to exponentially amplify polynucleotides is the well-known polymerase chain reaction (PCR). Isothermal amplification methods are another enzymatic technique. Isothermal methods typically employ unique DNA polymerases for separating duplex DNA. Isothermal amplification methods include Loop-Mediated Isothermal Amplification (LAMP), Whole Genome Amplification (WGA), Strand Displacement Amplification (SDA), Helicase-Dependent Amplification (HDA), Recombinase Polymerase Amplification (RPA), and Nucleic Acid Sequences Based Amplification (NASBA). See Yongxi Zhao, et al., *Isothermal Amplification of Nucleic Acids*, Chemical Reviews, 115 (22), 12491-12545 (2105) for a discussion of isothermal amplification techniques.

However, creating multiple copies of the synthetic polynucleotides 104 is not necessary in some implementations. Polynucleotide strands may be recovered following most sequencing procedures even though they are typically discarded. Thus, it is possible to generate only one copy of each of the synthetic polynucleotides with random sequences then sequence and recover the polynucleotide strands. Doing so places the same molecules that were sequenced on the item 102 as the anti-counterfeit tag 100. Moreover, future sequencing technologies may not discard the polynucleotide strands following sequencing (e.g., in situ sequencing).

If sequencing is performed, at least some of the synthetic polynucleotides 104 are sequenced. As described above, a subset of the synthetic polynucleotides 104 following the creation of multiple copies of each of the synthetic polynucleotides, may be used for sequencing. This subset may include a sufficiently sized sample that, given the number of copies of each unique polynucleotide strand and the concentration of the polynucleotide strands, there is a high probability of containing at least one copy of each unique polynucleotide strand. There may be a nearly 100% probability that the subset contains unique polynucleotides strands that represent some percentage (e.g., 99.9%, 99%, 95%, or 90%) of the total number of unique polynucleotide strands that were synthesized.

Sequencing may be performed by any current or later-developed technique for polynucleotide sequencing such as sequencing-by-synthesis or nanopore sequencing. Techniques for sequencing polynucleotides are well known to those of ordinary skill in the art. Sequences of the synthetic polynucleotides 104 of the anti-counterfeit tag 100 are referred to as original sequences. The original sequences refer to a representation of the nucleoside bases in the synthetic polynucleotides 104 such as, for example, an electronic file containing text strings of single-letter representations of nucleoside bases (i.e., A, G, C, and T). As discussed above, there may be some synthetic polynucleotides 104 that are not sequenced and thus are not represented in the original sequences. However, when dealing with very large numbers of synthetic polynucleotides 104 (e.g., millions or billions) essentially all of the synthetic polynucleotides 104 will be sequenced and included in the original sequences. Thus, there may be essentially the same number of sequence strings in original sequences as the number of synthetic polynucleotides 104 with unique random sequences.

If the synthetic polynucleotides 104 are sequenced, the original sequences may be transmitted to an electronic record 108. The ratios of nucleoside bases 106 are transmitted to the electronic record. This may be referred to as registering the ratios of nucleoside bases 106 of the anti-counterfeit tag 100. The electronic record 108 may be a database or other system for storing and organizing electronic data. The ratios of nucleoside bases 106 may be encrypted or otherwise protected in the electronic record 108 to prevent unauthorized access. In some implementations, a hash of the ratios of nucleoside bases 106 rather than a list of the ratios themselves is stored in the electronic record 108.

In some implementations, the electronic record 108 may be maintained by one or more computing devices 110 that are physically distant from the polynucleotide sequencer that generated the original sequences and physically distant from the item 102. For example, the electronic record 108 may be maintained by a network server or in a "cloud" implementation maintained in redundant format by multiple different pieces of hardware connected to a network such as the Internet. The electronic record 108 may be maintained by a third party that is not directly involved in any transactions with the item 102.

The original sequences stored in the electronic record 108 may be used as an additional check on the validity of the anti-counterfeit tag 100. If a bad actor identified that nucleotide base ratios rather than the sequences are used to authenticate the item 102, it would be relatively easy to create a set of random polynucleotides with the same ratios of nucleoside bases but different sequences. Thus, to confirm validity of an anti-counterfeit tag 100 the sequences of some portion of the synthetic polynucleotides 104 may be checked in addition to the ratios of nucleoside bases 106.

Although it is possible to create a different set of synthetic polynucleotides 104 with the same ratios of nucleoside bases, the large number of synthetic polynucleotides 104 make recreating the same sequences by non-random synthesis expensive. Although the synthetic polynucleotides 104 were created by a process that generates random sequences, those same sequences cannot be regenerated by another random synthesis. To recreate the synthetic polynucleotides 104, a bad actor would have to perform one synthesis run for each of the thousands, millions, or even billions of unique random sequences included in the synthetic polynucleotides 104.

For example, it may cost the legitimate creator of the anti-counterfeit tag 100 about $9 to synthesize 1 trillion polynucleotides with random sequences but it would cost $9×1 trillion or $900 trillion to synthesize each of those unique sequences individually. While parallelized, array-based polynucleotide synthesis is capable of decreasing the per-strand cost, modern techniques produce on the order of 1 million unique polynucleotides per parallelized synthesis. Even with this scaling considered, it would still require a cost premium on the order of a million times to counterfeit the pool of 1 trillion polynucleotides considered above. Thus, it may be prohibitively expensive for a bad actor to use de novo synthesis to reproduce a large number of synthetic polynucleotides 104 with the same random sequences.

If included in the electronic record, the original sequences may be made publicly available. However, the fact that the specific base ratios at each position are used to validate the authenticity of the item 102 may be kept secret. Therefore, although the base ratios can be calculated from analysis of the original sequences, a bad actor would have no motivation to determine the base ratios at each position in the original sequences.

The authenticity of the item 102 can be determined by collecting the synthetic polynucleotides 104 from the item 102. The number of polynucleotides 104 placed on the item 102 may be many fewer than the total number synthesized. For example, the number of polynucleotides 104 placed on the item may be in the hundreds (e.g., about 100, 200, 300, 400, 500, 600, 700, 800, or 900) or thousands (e.g., about 1000, 2000, 3000, 4000, 5000, 6000, 7000, 8000, or 9000). In some implementations, a much larger number of polynucleotides 104 may be placed on the item such as about $10^8$, $10^9$, $10^{10}$, $10^{11}$, or $10^{12}$.

If the synthetic polynucleotides 104 of the anti-counterfeit tag 100 are placed on a specific location on the item 102, that location may also be included in the electronic record 108 to guide collection of the polynucleotides 104. The synthetic polynucleotides 104 may be collected from the item 102 by swabbing the surface, removing a portion of the item 102 and extracting the polynucleotides, rinsing the item 102 and extracting the polynucleotides from the rinse solution, or by another technique. Many techniques and commercial kits for collecting, purifying, preparing samples for sequencing are known to those of ordinary skill in the art. For example, techniques developed for environmental or forensic samples may be used to collect and process the synthetic polynucleotides 104 collected from the item 102. See Hinlo R., Gleeson D., Lintermans M., Furlan E. (2017) *Methods to maximise recovery of environmental DNA from water samples*. PLoS ONE 12(6) and Butler, John M. *Forensic DNA Typing—Biology, Technology, and Genetics of STR Markers*" Second Edition, Elsevier Academic Press, Burlington, MA (2005).

The synthetic polynucleotides 104 collected from the item 102 are provided to a sequencer 112 and sequenced. In some implementations, the synthetic polynucleotides 104 may be processed by techniques known to those of ordinary skill in the art to prepare the sample for sequencing. For example, the polynucleotides collected from the item 102 may be cleaned or have impurities removed. The number of copies of the synthetic polynucleotides 104 may be further increased by techniques such as PCR. The sequencer 112 may be any type of device that can detect the nucleotide base sequence of polynucleotides.

In some implementations, only a portion of the synthetic polynucleotides 104 are sequenced. Sequencing fewer than all of the synthetic polynucleotides 104 collected from the item 102 results in a lower sequencing cost while still providing enough sequences to determine the ratio of nucleoside bases at each position. For example, a subsample of the synthetic polynucleotides 104 collected from item 102 may be used for sequencing without sequencing the remainder of the sample. The portion of the synthetic polynucleotides 104 may be selected randomly such as by taking an aliquot of the polynucleotides. As used herein, a portion of the synthetic polynucleotides 104 can mean fewer than 1%, about 1%, fewer than 10% or about 10% of the total number of synthetic polynucleotides 104 recovered from the item 102. A substantial portion of the synthetic polynucleotides 104 means at least about 50% of the total number of synthetic polynucleotides 104 recovered from the item 102.

A portion of the synthetic polynucleotides 104 is more than one polynucleotide and may include at least 100 polynucleotides, at least 1,000 polynucleotides, at least 10,000 polynucleotides, or at least 100,000 polynucleotides. In some implementations, the size of the portion (and thus the cost of sequencing) may be based on a value of the item 102. For example, the size of the portion may be selected such that the cost of sequencing is about 0.01%, about 0.1%, about 0.5%, about 1%, about 2%, about 3%, about 4%, or about 5% of the value of the item.

In some implementations, the sequencer 112 may be a nanopore sequencer. Nanopore sequencing reads the sequence of nucleoside bases on a single-stranded oligonucleotide by passing the oligonucleotide through a small hole of the order of 1 nanometer in diameter (a nanopore). Immersion of the nanopore in a conducting fluid and application of a potential across the nanopore results in a slight electrical current due to conduction of ions through the nanopore. The amount of current that flows through the nanopore is sensitive to the size of the nanopore. As an oligonucleotide passes through a nanopore, each nucleotide base obstructs the nanopore to a different degree. This results in a detectable change in the current passing through the nanopore allowing detection of the order of nucleoside bases in an oligonucleotide. See Branton, Daniel, et al. "The potential and challenges of nanopore sequencing." *Nanoscience and technology: A collection of reviews from Nature Journals* (2010): 261-268. One example of a nanopore sequencer is the Oxford Nanopore MinION® sequencer.

The sequencer 112 may be connected to a computing device 114. The computing device 114 may be any type of conventional computing device such as a laptop computer, a desktop computer, a tablet, or the like. In some implementations, the sequencer 112 and the computing device 114 may be integrated into a single device. The sequencer 112 and the computing device 114 may be operated by a purchaser or potential purchaser of the item 102. Thus, by use of publicly available tag descriptions in the electronic record 108 and compact sequencers 112 such as nanopore sequencers the techniques of this disclosure provide a way for purchasers to independently determine the authenticity of the item 102.

The sequencer 112 together with the computing device 114 generate one or more electronic files representing the order of nucleoside bases in the synthetic polynucleotides 104. These sequences output from the sequencer 112 are referred to as retrieved sequences 116. The retrieved sequences 116 are provided to the computing device 110 communicatively connected to the electronic record 108. In some implementations, the computing device 114 connected to the sequencer 112 and the computing device 110 communicatively connected to the electronic record 108 are in communicative connection with each other via a network such as the Internet.

The computing device 110 may calculate base ratios from the retrieved sequences 116. These ratios determined from the retrieved sequences 116 are referred to as "calculated base ratios" to differentiate from the ratios of nucleoside bases 106 that were used to synthesize the synthetic polynucleotides 104. The calculated base ratios are compared to the ratios of nucleoside bases 106 to determine if they are the same or have at least a threshold level of similarity.

In many implementations, this will involve first aligning thousands, millions, or more sequence strings each with potentially hundreds of bases and then determining base ratios for each position in the alignment. This may require a significant number of computational operations to perform the alignments and calculate the base ratios in a short amount of time such as less than five minutes, less than one minute, less than 30 seconds, or less than 10 seconds. Thus, utilizing cloud resources or network devices such as the electronic record 108 and the computing device 110 removes the computational burden from the computing device 114. This allows users with a computing device 114 with less processing power to promptly receive a determination of authenticity of the item 102. If there is a match, then an indication of authenticity 118 is returned from the computing device 110 to the computing device 114. The computing device 114 may then display a notification to a user that the item 102 is authentic. If the calculated base ratios do not match the ratios of nucleoside bases 106, the computing device 110 may return an indication that the item 102 is not authentic or that the validation failed.

If the item 102 is authentic, the synthetic polynucleotides 104 are the same polynucleotides placed on the item when it was initially tagged. However, damage to the synthetic polynucleotides 104 while placed on the item 102 and errors in synthesis and sequencing may result in the retrieved sequences 116 being different from the original sequences. Subsampling to create the retrieved sequences 116 may also slightly alter the ratios of nucleotide bases at each position. Most of the errors are expected to be distributed randomly, so if there is a large number of sequences (i.e., millions or more) the presence of some errors will not appreciably change the calculated base ratios.

Because the ratios of nucleoside bases are compared rather than the actual sequences themselves, this technique is robust to many types of errors. The calculated base ratio determined from the retrieved sequences 116 may be considered to match the predetermined base ratio of the original sequences if the two ratios have at least a threshold level of similarity. For example, if the expected base ratio was 50% A and 50% T but the detected base ratio was 52% A and 48% T those two different ratios may be determined to "match" because there within a threshold level of similarity (e.g., 2% in this example). The threshold level of similarity may be determined experimentally and could be any value that is useful for distinguishing the actual synthetic polynucleotides 104 from another set of random polynucleotides. For example, the threshold level of similarity could be within 0.1%, 1%, 5%, 10%, 20%, or a different threshold. The threshold level of similarity required may be based on the type of protection for the synthetic polynucleotides 104, the length of time since the item 102 was tagged with the synthetic polynucleotides 104, the sequencing technique, and/or the value of the item 102.

Figure 2A:
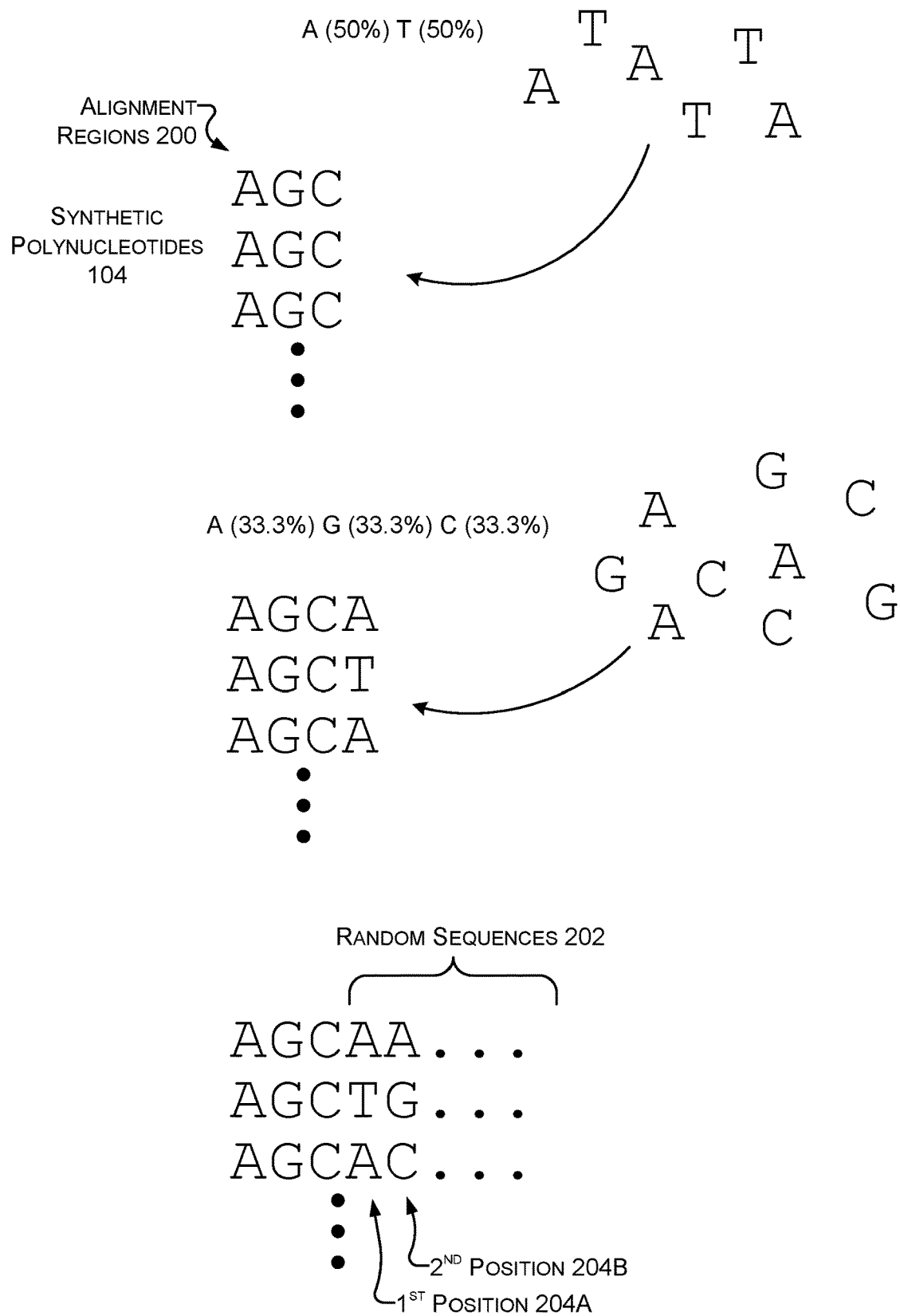
FIG. 2A illustrates creation of synthetic polynucleotides with alignment regions and random sequences having specific, predetermined ratios of nucleoside bases.

FIG. 2A illustrates creation of synthetic polynucleotides 104 with alignment regions 200 and random sequences 202 having specific, predetermined ratios of nucleoside bases. The synthetic polynucleotides 104 may be created with any technique for creating polynucleotides that can produce a population of nucleotides with specific ratios of nucleoside bases at each position.

The synthetic polynucleotides 104 may include alignment regions 200 that are not random. The alignment regions 200 may be the same in all of the synthetic polynucleotides 104. There may also be differences or variations in the alignment regions 200 between individual ones of the synthetic polynucleotides 104. The alignment regions 200 may have a role in the synthesis of the synthetic polynucleotides 104. For example, the alignment regions 200 may be linker sequences used in solid-phased synthesis or initiator sequences used for enzymatic synthesis. The alignment regions 200 may be of any length but are typically shorter than the random sequences 202. For example, the alignment regions 200 may be between about 5-40 nucleotides long such as, for example, about 10, about 20, about 30, or about 40 nucleotides long. The synthetic polynucleotides 104 may also lack alignment regions 200 and be only random sequences 202.

The alignment regions 200 may be primer binding sites designed to hybridize with PCR primers. Techniques for designing PCR primers and techniques for evaluating the suitability of primer sequences are well known to persons of ordinary skill in the art.

Synthesis of the synthetic polynucleotides 104 may proceed by extending the alignment regions 200 with multiple rounds of nucleoside addition in which nucleotides with a mixture of different bases are added. In this example, a first round of addition uses a mixture of 50% A and 50% T. This creates a population of polynucleotides strands in which 50% of the strands will have an A at this position and 50% of the strands will have a T. Although only three polynucleotide strands are shown, in practice many more strands will be synthesized simultaneously such as $10^4$ to $10^{24}$ strands. Next an equal mixture of polynucleotides with A, G, or C as the base is added. Cycles of addition continue extending the random sequences 202. The ratio of nucleoside bases added during each cycle may vary from only a single nucleoside base (e.g., 100% C) to an equal amount of each nucleoside base (25% A, 25% G, 25% C, 25% T) or some other ratio of two, three, or four different nucleoside bases. The ratio of individual nucleoside bases is varied over individual rounds of addition such that is not the same ratio used for the entire length of the random sequences 202.

Positions 204 in the random sequences 202 may be identified relative to the alignment regions 200 or relative to an alignment of the synthetic polynucleotides 104 without alignment regions 200 based on 3'-end or 5'-end of the sequences. For example, a first position 204A may be the nucleotides added to the synthetic polynucleotides 104 directly adjacent to the alignment regions 200. Alternatively, the first position 204A may be the most distal 3'-end or the most distal 5'-end nucleoside. A second position 204B may be the next set of nucleosides adjacent to the first position 204A.

A total length of the individual synthetic polynucleotides 104, and thus a length of the random sequences 202, may depend on the technique used to synthesize the polynucleotides. Phosphoramidite synthesis can synthesize polynucleotides accurately to a maximum length of about 300 nucleotides. See Palluk, S., Arlow, D. H., Rond, T., de, Barthel, S., Kang, J. S., et al. (2018). De novo *DNA synthesis using polymerase-nucleotide conjugates*. Nat. Biotechnol. 36, 645-650. Thus, the random sequences 200 may have a length of about 100-300 nucleotides, about 100 nucleotides, about 150 nucleotides, about 200 nucleotides, about 250 nucleotides, or about 300 nucleotides. Improvements in phosphoramidite synthesis technology may increase this maximum length above 300 nucleotides.

Enzymatic polynucleotide synthesis can create polynucleotides that are many thousands of nucleotides long. See Tang L, Tjong V, Li N, Yingling Y G, Chilkoti A, & Zauscher S (2014). *Enzymatic polymerization of high molecular weight DNA amphiphiles that self-assemble into star-like micelles*. Advanced Materials, 26(19), 3050-3054. Synthetic polynucleotides 104 synthesized by enzymatic synthesis may have a range of lengths due to variations in the number of polynucleotides incorporated at different strands by the enzymatic synthesis process. Thus, synthetic polynucleotides 104 synthesized by an enzymatic method may be described as having one average length although there will be variations in length for some of the individual polynucleotides. In some implementations, the average length of the synthetic polynucleotides 104 is greater than 400 nucleotides. For example, the average length of the synthetic polynucleotides 104 may be about 1000 nucleotides, about 5000 nucleotides, about 10,000 nucleotides, or another length greater than 400 nucleotides.

Figure 2B:
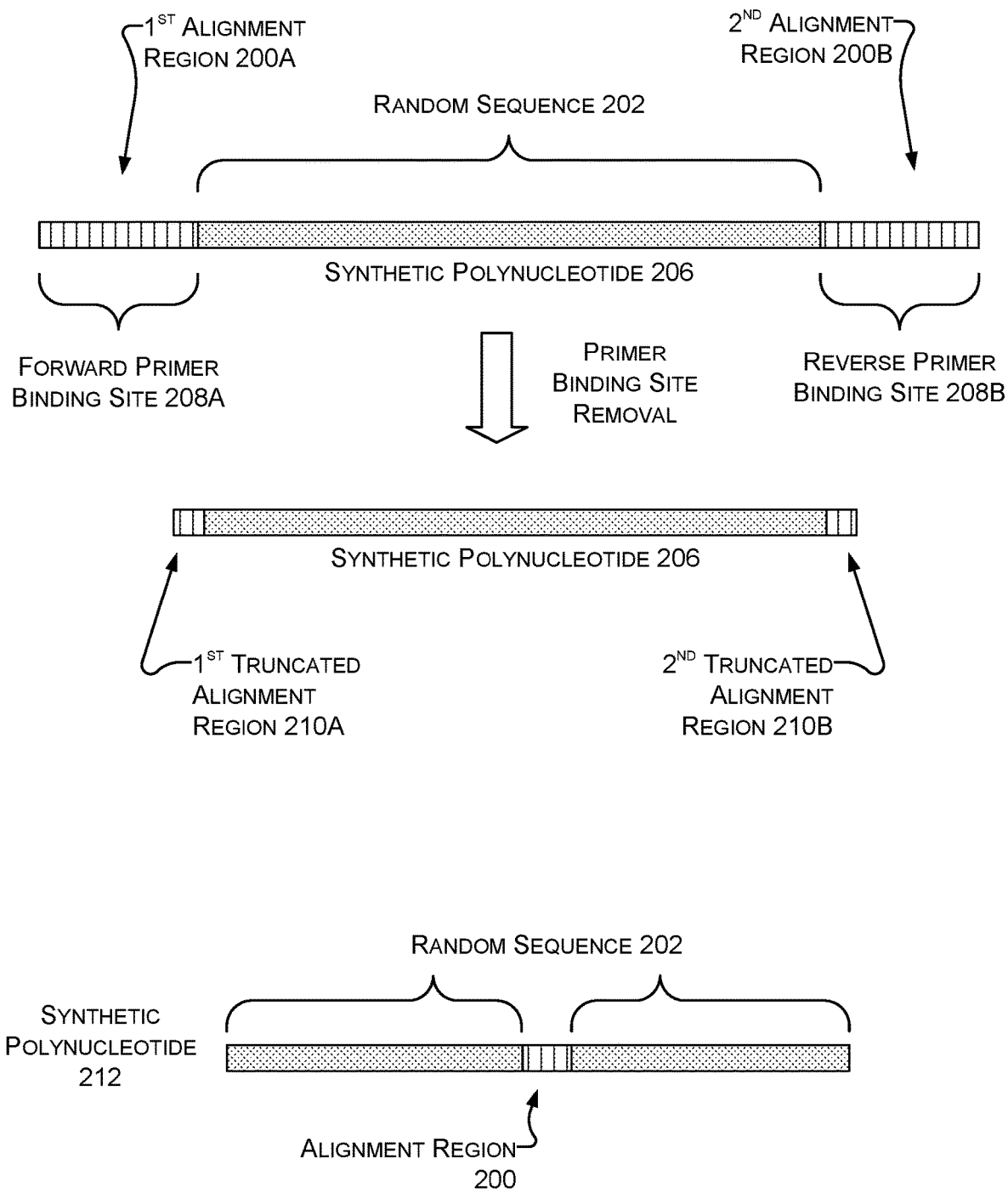
FIG. 2B illustrates schematic representations of a synthetic polynucleotide with primer binding sites on the ends that are shortened and a synthetic polynucleotide with an alignment sequence located in the middle of a random sequence.

FIG. 2B shows example arrangements of alignment regions 200 and random sequences 202 in synthetic polynucleotides. One example structure for a synthetic polynucleotide 206 has a first alignment region 200A at one end and a second alignment region 200B at the other end. In one example configuration, the first alignment region 200A is a forward primer binding site 208A and the second alignment region 200B is a reverse primer binding site 208A. In some implementations, all of the synthetic polynucleotides 104 may have the same forward and reverse primer binding sites. This makes it possible to use a single set of primers to PCR amplify the entire set of synthetic polynucleotides 104.

However, having one or a few sets of primer binding sites 208 for the entire population of synthetic polynucleotides 104 makes it possible to easily copy the synthetic polynucleotide 104 with PCR. A bad actor who learns of the primer sequences could then obtain an item labeled with an anti-counterfeit tag 100 and make a copy of all or most of the synthetic polynucleotides 104. This copy would likely have the same ratios of bases at each position and could be used as a fake tag.

To prevent this, the primer binding sites 208 may be removed or truncated so that they can no longer function as primer binding sites 208. There are many techniques known to those of ordinary skill in the art for cleaving the ends of polynucleotides that have known sequences. This can be done, for example, by enzymatic digestion such as USER digest, restriction enzyme digestion, RNA digestion, UV cut, or other technique.

For example, the primers may include deoxy-uracil to introduce uracil bases at the junction of the primer binding site 208 to the random sequence 202. The USER digest breaks the phosphodiester backbone of a polynucleotide by using a uracil cleavage system in which the sequential addition of Uracil DNA Glycosylase (UDG) and endonuclease VIII generates a single nucleotide gap at the location of a uracil base in polynucleotide containing a deoxy-uracil. UDG catalyzes the excision of the uracil base, creating an abasic site with an intact phosphodiester backbone. The lyase activity of Endonuclease VII breaks the phosphodiester backbone both 3' and 5' to the abasic site, liberating the deoxyribose sugar.

As a further example, the primer binding sites 208 may be designed with sequences that are recognized and cleaved by a restriction endonuclease. If the primer binding sites 208 are not fully removed, they may be truncated to create a first truncated alignment region 210A and a second truncated alignment region 210B. The first truncated alignment region 210A and the second truncated alignment region 210B contains a short non-random sequence (e.g., 1-5 nucleosides) that is not long enough to function as a primer binding site 208.

An alignment region 200 may also be included within a random sequence 202 as illustrated in synthetic polynucleotide 212. The alignment region(s) 200 if present may be at any location in the synthetic polynucleotide 212 not only at the ends. The alignment region 200 may be positioned in the middle of the random sequence 202 so that it is equal distance from both ends of the molecule or it may be located someplace other than the middle. There may be multiple alignment regions 200 in the synthetic polynucleotide 212.

Figure 3:
FIG. 3 illustrates an entry in an electronic record used for determining the authenticity of an item tagged with synthetic polynucleotides and examples of composite letters.

FIG. 3 shows an example entry 300 in the electronic record 108. As described above, the electronic record 108 may be maintained on one or more network-accessible computing devices at one or more locations physically distant from the item (i.e., a cloud-based system). Each entry 300 in electronic record 108 may include the ratios of nucleoside bases 106. If the synthetic polynucleotides are 150 nucleosides long, ratios of nucleoside bases 106 will include an ordered series of 150 ratios. The electronic record 108 may also include one or more of the full original sequences 302 of the synthetic polynucleotides, a barcode 304 encoded by the ratios of nucleoside bases 106, and a description of the item 306. The electronic record 108 may include entries for multiple different items. In some implementations, the electronic record 108 may be implemented as a list, a table, an array, a spreadsheet, a database, or another data structure.

The original sequences 302 may be in any electronic format used for storing representations of polynucleotides such as American Standard Code for Information Interchange (ASCII) or FASTA. Although only three partial sequences are shown in FIG. 3, the original sequences 302 will in most implementations include a much larger number of unique sequences (e.g., $10^4$ or more) each with lengths of about 100 or more nucleotides such that manipulation other than by a computer would be impractical or impossible.

The ratio of nucleoside bases 106 indicates the ratio or percentage of the nucleoside bases found across the population of synthetic nucleotides at each position in the random sequences. This may be represented as a table or an array that includes an entry for the position in the random sequences followed by an entry indicating the percentage or relative amount of each of the nucleoside bases. The table illustrating FIG. 3 may also be represented as (50, 0, 0, 50); (33, 33, 33, 0); (0, 25, 75, 0); (0, 0, 0, 100); . . . where the numerical values represent percentages of nucleoside bases is listed the order A, G, C, T. Similar representations may be used to record the ratio of nucleoside bases in polynucleotides of any length. Thus, the ratio of nucleoside bases 106 describes a characteristic of the population of synthetic polynucleotides 104 as a whole rather than the sequence or percentage of nucleosides included in any individual polynucleotide. The ratios of nucleoside bases 106 are maintained in secret and not made available to those who access the electronic record 108. In some implementations, the ratios of nucleoside bases 106 may be accessible only to computing devices that manage operation of the electronic record 108 such as the computing device 110 shown in FIG. 1. The ratios of nucleoside bases 106 may also be protected by encryption or by conversion to a hash value.

The barcode 304 may be a numerical representation in binary, Arabic numerals, ASCII characters, or other format used to uniquely identify the item 102. The barcode 304 is encoded in the ratios of nucleoside bases 106. One way to encode a barcode 304 is by creating mappings between the ratios of nucleoside bases 106 and composite letters. Each composite letter represents a specific value that may be, but is not limited to, one or more bits. In some implementations, the entry 300 may include only the barcode 304 without the ratios of nucleoside bases 106 or even the original sequences 302. The barcode 304 may be encrypted or stored as a hash value. Thus, in some implementations, the entry 300 may contain only a hash of the barcode 304 and the description of the item 306. The retrieved sequences 116 may be processed by the computing device 110, or another computing device, to derive the composite letters and determine if the retrieved sequences 116 encode the barcode 304 or not.

The description of the item 306 may include, for example, a photograph 308 and/or the text description 310 of the item. Other types of descriptions of the item 306 are also possible such as, for example, a description of another taggant placed on the item such as a serial number or code. The description of the item 306 is used to identify the item tagged with the synthetic polynucleotides 104.

The ratios of nucleoside bases 106 can be registered in the electronic record 108 with the description of the item 306 even before the synthetic polynucleotides 104 are sequenced. If the synthetic polynucleotides 104 are sequenced, the original sequences 302 can be added to the entry 300. If a barcode 304 is used for the anti-counterfeit tag 100, that barcode 304 may be determined and saved in the electronic record 108 prior to synthesis of the synthetic polynucleotides 104. Entry 300 may be registered in the electronic record 108 by uploading at least one of the original sequences 302, the ratios of nucleoside bases 106, and the barcode 304 together with a description of the item 306. The description of the item 306 may be uploaded from the same or a different computing device. The original sequences 302, ratios of nucleoside bases 106, barcode 304, and the description of the item 306 may be uniquely linked, associated, joined, or correlated in the electronic record 108 with each other.

The entry 300 may also include a description of where the synthetic polynucleotides 104 are located on the item 102. For example, the entry 300 may describe where on the outside surface of the item 102 the synthetic polynucleotides 104 were placed. If the item 102 is liquid, the entry 300 may indicate that the synthetic polynucleotides 104 are included in the liquid rather than on a container. This can guide collection of the polynucleotides for the purpose of validating the authenticity of the item 102.

Table 312 illustrates a correlation between composite letters 314 and binary values 316. Composite letters 314 are representations of a position in a sequence that consists of a mixture of all four nucleotides in a predetermined ratio. This in effect limits the choices for possible ratios of the nucleoside bases to one of a discrete set of ratios. These choices are implemented at the time of polynucleotide synthesis by selecting the ratio nucleotides provided to the synthesis hardware. Composite letters are discussed in the context of DNA data storage in Anavy, L., and Vaknin, I., et al. *Data storage in DNA with fewer synthesis cycles using composite DNA letters*. Nat Biotechnol 37, 1229-1236 (2019).

In this example, each of the composite letters 314 is an equal mixture of two different nucleoside bases. Other ratios and ratios using only one or more than two different nucleoside bases are also possible. The number of unique letters defines the size of the alphabet. In this example, there are four composite letters 314 so the size of the alphabet is four. Smaller or larger alphabets are also possible.

Each of the composite letters 314 may be correlated or mapped to another value such as one of the binary values 316. Thus, in this example, a ratio of nucleoside bases that is 50% T and 50% C represents the binary value 11. With this encoding scheme, any binary number may be represented by the ratios of nucleoside bases in the synthetic polynucleotides 104. Thus, in an implementation, the anti-counterfeit tag 100 may be represented as a binary number that is encoded in the synthetic polynucleotides 104 according to the composite letters 314 and recorded in the electronic record 108 as the barcode 304.

Writing a composite letter 314 at a given position of the synthetic polynucleotides 104 is equivalent to synthesizing multiple polynucleotides with different sequences so that in this given position the different nucleoside bases are distributed across the synthesized copies according to the ratio indicated by the composite letter 314. Reading a composite letter 314 includes the sequencing of multiple independent molecules representing the same composite sequence and inferring the original ratio or composition from the observed base frequencies.

Reading a composite letter 314 may also include identifying the best matching letter by comparing the actual percentages of nucleoside bases detected to the ratio of bases for each of the composite letters 314 in the alphabet. For example, consider one composite letter that is 50% G and 50% C and a second composite letter that is 25% G and 75% C. If the detected ratio of nucleoside bases in the retrieved sequences at this position is 40% G and 60% C, that does not match either of those two composite letters 314. However, because it is closer to the ratio represented by the composite letter of 50% G and 50% C it can be identified as such. Thus, when the ratio of nucleoside bases is constrained to one of several composite letters 314 in an alphabet, the actual percentage of nucleoside bases as identified from the retrieved sequences 116 is first translated to a one of the composite letters 314. Then that composite letter is compared with the composite letter 314 encoded at that same position in the original sequences.

The composite letters 314 may be created so that there is a minimum level of orthogonality between each letter. If an alphabet contains two composite letters 314 with similar ratios of nucleoside bases it could be difficult to determine which letter best corresponds to an ambiguous ratio of nucleoside bases. Thus, to make sure each of the composite letters 314 in any given alphabet are distinguishable from one another they may be designed such that there is at least some minimum amount of difference in the percentages or ratios of one or more nucleoside bases.

For example, an alphabet of composite letters 314 could be designed such that the percentage of at least one nucleoside base in each letter varies from all the other letters in the alphabet by a threshold amount such as 25%. Thus, there will be no two composite letters 314 in the alphabet for which the relative amounts of all nucleoside bases are less than 25% (or some other threshold) different from each other. For example, consider the composite letters (50% A, 0% G, 0% C, T 50%) and (25% A, 25% G, 25% C, 25% T). These two letters are sufficiently orthogonal according to the 25% threshold because there is at least one base (actually all four bases) that has at least a 25% difference in the relative percentages. However, the composite letters (20% A, 30% G, 0% C, 50% T) and (30% A, 20% G, 0% C, 50% T) would not be considered sufficiently different from each other because the relative percentages of all of the four bases are within 25%. Other thresholds for the predetermined ratios of nucleoside bases for each composite letter may be used besides 25% such as, for example, 50% or 75%.

Figure 4:
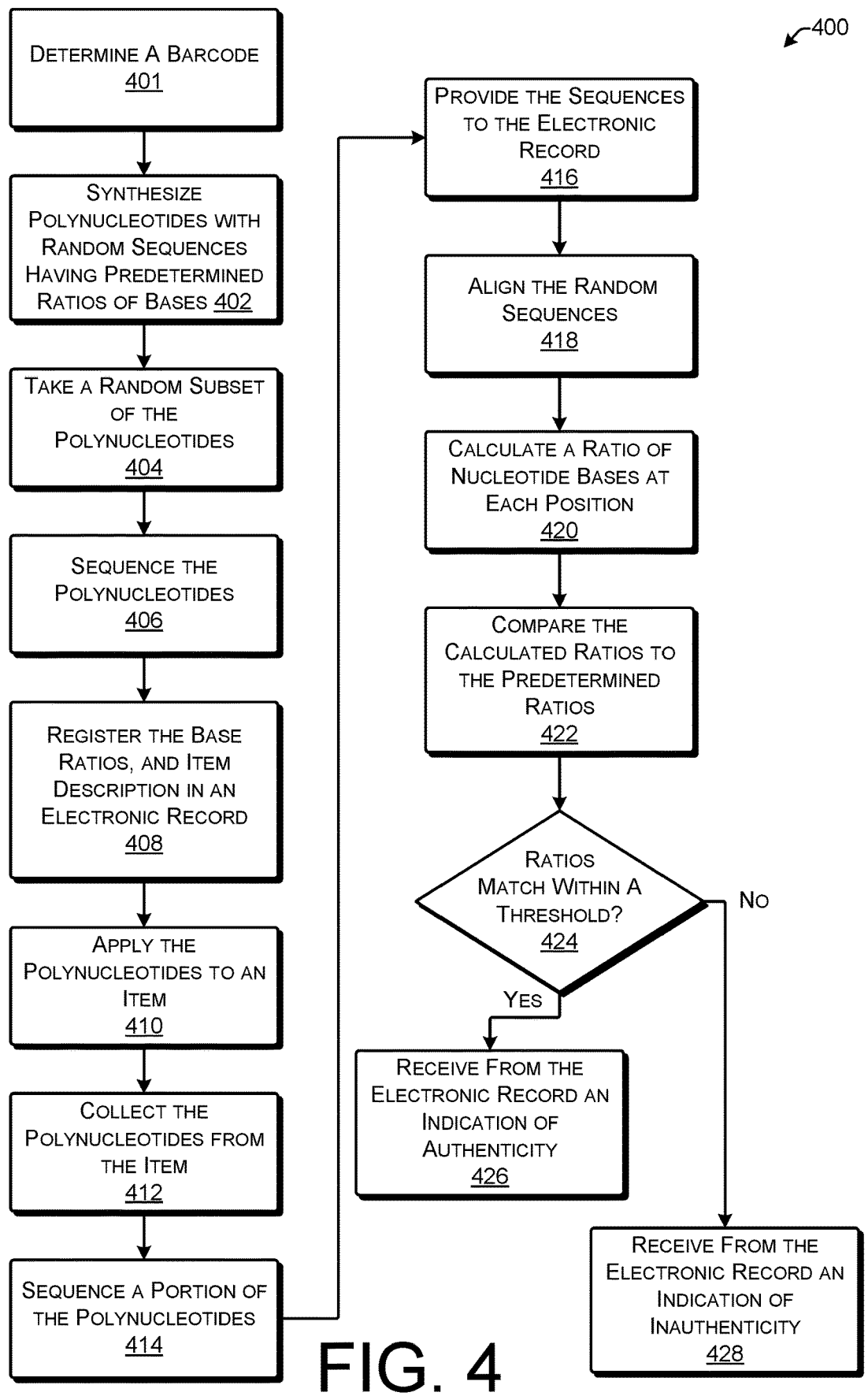
FIG. 4 is a flow diagram showing an illustrative process for using synthetic polynucleotides as an anti-counterfeit tag.

FIG. 4 shows an illustrative process 400 for tagging an item with an anti-counterfeit tag made from a plurality of polynucleotides having random sequences with a specific, predetermined ratio of nucleoside bases at each position in the random sequences.

At operation 401, a barcode may be determined. The barcode can be a unique identifier used to indicate that an item labeled with the barcode is authentic. The barcode may be represented as a string of bits, Arabic numerals, letters, ASCII characters, or another way. The barcode may be determined in advance of synthesizing the polynucleotides to tag the item.

At operation 402, a plurality of synthetic polynucleotides comprising random sequences with a specific, predetermined ratio of nucleoside bases at each position in the random sequences is synthesized. The polynucleotides may be synthesized by any technique that creates DNA or RNA strands such that at least a portion of the strands have a random sequence of nucleoside bases and that the ratio of nucleoside bases incorporated can be controlled. Techniques are known to those of ordinary skill in the art for synthesizing polynucleotides with random sequences having specific ratios of bases and include phosphoramidite synthesis and enzymatic synthesis. One technique for creating a large number of polynucleotides with random sequences is column synthesis using the phosphoramidite method. Synthesis will generally create one copy of each polynucleotide with a unique random sequence.

During synthesis of random polynucleotides, individual nucleosides are mixed prior to entering a solid state binding substrate, where they start forming a polynucleotide strand based on their coupling efficiencies. The rate of the individual nucleotides couplings, $r_i$, can be approximated by multiplication of the respective rate constant, $k_i$ and the nucleotide concentration, $c_i$. During the process, individual nucleotides are shielded from binding to other nucleotides using protecting groups, ensuring that only one new random nucleotide can bind per polynucleotide strand per iteration. Excess nucleotides that have not found a polynucleotide strand to bind to are then removed from the synthesis chamber, and polynucleotide strands are de-protected. To elongate each polynucleotide strand to the desired length, the process of adding a mix of nucleotides, washing off left-over and subsequently de-protecting is repeated as often as required. Once the desired strand length of polynucleotides has been reached, the polynucleotides are cleaved from the synthesis support.

The specific ratio of bases on the nucleoside phosphoramidites or nucleoside triphosphates provided for each round of addition is controlled to achieve the specific, predetermined ratio. The next base incorporated in any given strand during a round of synthesis will be determined stochastically according to the relative availability of nucleotides with each of the different bases. For example, the synthetic polynucleotides may be created by phosphoramidite synthesis with a ratio of individual nucleoside bases that is varied over individual rounds of phosphoramidite addition. Alternatively, the polynucleotides may be created by enzymatic single-base-addition synthesis with a ratio of individual nucleoside bases that is varied over individual rounds of nucleotide addition. Polynucleotides created in this way have sequences that are not specified in advance and have an order of nucleoside bases that is random for each molecule. However, at each position in the collection of polynucleotides there is a specific ratio of bases. These predetermined ratios of bases vary across the positions of the random sequences so that when multiple polynucleotides are analyzed they encode a specific nucleoside base ratio at each position.

The specific, predetermined ratio of nucleoside bases at each position in the random sequences may be one of several predetermined ratios representing composite letters. Each of the predetermined ratios represents a different composite letter and the composite letters are mapped to values such as binary digits. In some implementations, the composite letters are formed from at least two different nucleoside bases so that none of the composite letters are 100% of a single base. The number of different composite letters in an alphabet and the specific ratios of nucleoside bases for each composite letter are determined in advance. In some implementations, the composite letters may be designed so that there is a level of dissimilarity or orthogonality between the ratios of nucleoside bases used for each letter. For example, each of the several predetermined ratios for the composite letters may vary from each other by at least a threshold difference in the amount of one, or more, of the nucleoside bases. For example, the threshold difference may be 25%, 50%, or 75%.

The plurality of synthetic polynucleotides may include a large number of polynucleotides such as many thousands, tens of thousands, hundreds of thousands, millions, or billions of different polynucleotides with unique, random sequences. A length of each of the synthetic polynucleotides may be between approximately 50 nucleotides and approximately 10,000 nucleotides. In some implementations, the synthetic polynucleotides may be synthesized by phosphoramidite synthesis, and a length of the synthetic polynucleotides may be about 100-300 nucleotides. In some implementations, the synthetic polynucleotides may be synthesized by enzymatic synthesis, and an average length of the synthetic polynucleotides may be greater than 400 nucleotides such as between about 400 and 10,000 nucleotides. Sequences with lengths shorter than 400 nucleotides may also be synthesized by enzymatic synthesis.

The synthetic polynucleotides may also include alignment regions that are non-random and share a same position in each of the plurality of synthetic polynucleotides relative to the random sequences. The alignment regions may be located at one or both ends (e.g., 3' end and/or 5'end) of the synthetic polynucleotides and/or inside the random sequences.

The alignment regions may be sequences that have a role in the synthesis of the polynucleotides. For example, the alignment regions may be linker sequences used to attach the polynucleotides to a solid substrate for solid-phase synthesis. As a further example, the alignment regions may be initiator sequences used by an enzyme such as TDT to initiate enzymatic synthesis and extension of the polynucleotide strands.

The alignment regions may alternatively or additionally have a role in later processing of the polynucleotides. For example, the alignment regions may be primer binding sites. The primer binding sites may be used for PCR amplification of the polynucleotides. In an implementation, each of the synthetic polynucleotides may include a forward primer binding site and a reverse primer binding site that are not random. Further, each of the synthetic polynucleotides may have the same forward primer binding site and reverse primer binding site so that all of the polynucleotides can be amplified with the same pair of primers. Design and use of polynucleotide primers are well known to persons of ordinary skill in the art. A length of the primer binding sites may be about 10-30 nucleotides and the non-random sequences may be designed using software and conventional techniques. Techniques for primer design are known to those of ordinary skill in the art.

At operation 404, a random subset of the plurality of synthetic polynucleotides generated at operation 402 may be taken for use as the anti-counterfeit tag. The random subset may be taken by dividing a sample containing the synthetic polynucleotides. For example, a sample of the polynucleotides may be divided into a first random subset and a second random subset by first diluting the synthetic nucleotides and then splitting the diluted polynucleotides into two equal volume portions. More than two random subsets may also be created.

Other techniques for generating a random subset include use of polynucleotide probes with random sequences anchored to magnetic beads. Although referred to as "random" subsets, it is not required that selection of the polynucleotides for includes in a subset is done in a manner that is strictly mathematically random. Ones of the synthetic polynucleotides that happen to have energy-positive interactions with the probes can be selectively captured on the magnetic beads. The energy-positive interactions cause some sequences of polynucleotides to be preferentially bound to the random sequences on the magnetic beads. The binding may be, but is not limited to, hybridization between reverse complementary single-stranded polynucleotides. The magnetic beads may then be separated from the remainder of the polynucleotides and the attached polynucleotides eluted to create a random subset.

Alternatively, a random subset may be created by PCR amplification with random primers that are, for example, about 5, 10, 15, or 20 nucleotides longs. This selectively amplifies those polynucleotides that have stronger interactions with the primers. It creates a population of polynucleotides in which the sequences that did not amplify are present at a much lower concentration and effectively removed from further processing because of the much higher concentration of the other polynucleotides that were amplified. Random primers, however, may hybridize to locations on the polynucleotides other than the ends creating multiple shorter sequences. Later matching would then use partial sequences rather than full-length sequences.

Taking a random subset of the plurality of synthetic polynucleotides is optional. If a random subset is not taken, all or substantially all of the synthetic polynucleotides generated at operation 402 may be used as the anti-counterfeit tag.

Taking a random subset from the synthesized polynucleotides produces a smaller number of polynucleotides that can be used for the anti-counterfeit tag. Thus, in some implementations, synthetic polynucleotides with random sequences may be synthesized in excess and only a portion of those synthetic polynucleotides are used to tag a specific item. Also, the synthetic polynucleotides synthesized at operation 402 may be divided into multiple random subsets and used to tag multiple different items. The cost of forging an anti-counterfeit tag depends on the length and number of polynucleotides that must be synthesized to reproduce the tag. There is less incentive to forge a counterfeit tag for lower value items than for higher value items. Accordingly, the number of synthetic polynucleotides in one or more random subsets used to tag an item may be based on the value of the item (i.e., more polynucleotides can be used to tag more expensive items).

At operation 406, at least a portion of the synthetic polynucleotides may be sequenced to obtain a plurality of original sequences. It is not, however, necessary to sequence the synthetic polynucleotides in all implementations because the predetermined ratios of nucleoside bases are known even without sequencing. All or fewer than all of the synthetic polynucleotides synthesized at operation 402 may be sequenced. For example, a large number of synthetic polynucleotides with random sequences may be synthesized by column synthesis and only a fraction of those may be sequenced (e.g., $10^{18}$ unique random sequences synthesized and $10^6$ sequenced). Multiple techniques and devices for sequencing polynucleotides are known to those of ordinary skill in the art including sequencing-by-synthesis and nanopore sequencing. The plurality of original sequences are representations of the nucleoside bases in the synthetic polynucleotides as detected by a sequencer. Sequencers are known to generate errors the type and frequency of which vary by type of sequencer and operational parameters. Thus, the plurality of original sequences may not perfectly represent the order of nucleoside bases in the synthetic polynucleotides.

If one or more random subsets of the synthetic polynucleotides is taken at operation 404, the polynucleotides in the one or more random subsets may be sequenced without sequencing the remainder of the synthetic polynucleotides generated at operation 402. Alternatively, only a portion of the entire batch of synthetic polynucleotides may be sequenced without taking a random subset. Thus, the undifferentiated set of synthetic polynucleotides may contain some nucleotide strands that are sequenced and some that are not.

Prior to sequencing, in some implementations, copies may be made of the synthetic polynucleotides so that there are multiple copies of each unique polynucleotide strand. An equal or approximately equal number of copies may be made of each unique polynucleotide strand so that the ratio of nucleoside bases is maintained across the entire population of polynucleotides. Once multiple copies of each unique strand exist, some polynucleotide strands can be sequenced and discarded while others are used to tag an item. Multiple copies of the polynucleotide strands may be made by any one of multiple techniques known in the art such as PCR, other enzymatic techniques, and non-enzymatic techniques for creating multiple copies of existing polynucleotides.

PCR refers to a reaction for the in vitro amplification of specific DNA sequences by the simultaneous primer extension of complementary strands of DNA. In other words, PCR is a reaction for making multiple copies or replicates of a target nucleic acid flanked by primer binding sites. The reaction comprising one or more repetitions of the following steps: (i) denaturing the target nucleic acid, (ii) annealing primers to the primer binding sites, and (iii) extending the primers by a template-dependent polymerase in the presence of nucleoside triphosphates. Usually, the reaction is cycled through different temperatures optimized for each step in a thermocycler. A thermocycler (also known as a thermal cycler, PCR machine, or DNA amplifier) can be implemented with a thermal block that has holes where tubes holding an amplification reaction mixture can be inserted. Other implementations can use a microfluidic chip in which the amplification reaction mixture moves via a channel through hot and cold zones.

Each cycle doubles the number of copies of the specific DNA sequence being amplified. This results in an exponential increase in copy number. Particular temperatures, durations at each step, and rates of change between steps depend on many factors well-known to those of ordinary skill in the art, e.g., exemplified by the references: McPherson et al., editors, *PCR: A Practical Approach and PCR 2: A Practical Approach* (IRL Press, Oxford, 1991 and 1995, respectively). Illustrative methods for detecting a PCR product using an oligonucleotide probe capable of hybridizing with the target sequence or amplicon are described in Mullis, U.S. Pat. Nos. 4,683,195 and 4,683,202; EP No. 237,362.

However, it is also possible in some implementations to recover the synthetic polynucleotides following sequencing. Thus, making additional copies would not be necessary and the same molecules that are sequenced will later be applied to an item as the anti-counterfeit tag. Following sequencing, synthetic polynucleotides that are recovered may be prepared for application to the item such as by cleaning or mixing with one or more stabilizing reagents.

If the synthetic polynucleotides are synthesized with primer binding sites, the primer binding sites may be removed or shortened following PCR amplification. This removes the primer binding sites from the synthetic polynucleotides placed on the item and prevents a bad actor from using PCR primers to copy all the polynucleotides in an anti-counterfeit tag. Any technique for removing nucleosides from the ends of a polynucleotide may be used such as USER digest, restriction enzyme digestion, RNA digestion, or UV cut.

At operation 408, a description of the item and the specific, predetermined ratio of nucleoside bases are registered in an electronic record. The electronic record may also contain the original sequences and/or a barcode for the item. In some implementations, the electronic record may contain the barcode but may not contain the original sequences or the specific, predetermined ratio of nucleoside bases. If included in the electronic record, the original sequences may be used as a secondary check for validity of an anti-counterfeit tag in addition to the ratios of nucleoside bases.

The registration may consist of creating an entry in the electronic record that links or otherwise associates one or more of the original sequences, the specific, predetermined ratio of nucleoside bases, and the barcode with the description of the item. The electronic record may also indicate where the synthetic polynucleotides are placed on the item. The electronic record may be a database, spreadsheet, table, list, or other data structure configured to store the original sequences and the description of the item. The electronic record may be maintained on a network-accessible computing device that is physically distant from the item and from any devices used to synthesize or sequence the polynucleotides. In an implementation, the electronic record may be maintained in a cloud-based system.

The electronic record may be publicly available so that the original sequences and description of the item may be accessed by anyone. If the electronic record only contains the barcode, that barcode sequence may be publicly available. However, the specific, predetermined ratio of nucleoside bases may be maintained in secret and not made publicly available. If it was publicly available, a bad actor could use a random synthesis technique to create a plurality of synthetic polynucleotides that have different sequences than the polynucleotides used in the actual tag but have the same ratios of nucleoside bases.

Access to the electronic record may be limited by any technique used to control access to an online database or electronic file. For example, the original sequences, ratios of nucleoside bases, and/or barcode may be encrypted or stored as a hash. For example, a username and password may be required to access the original sequences in the electronic record. This provides an additional level of security by making it more difficult for a bad actor to identify which polynucleotides need to be synthesized to forge the anti-counterfeit tag.

At operation 410, the plurality of synthetic polynucleotides is applied to the item. If a random subset of the synthetic polynucleotides is taken at operation 404, the polynucleotides in that random subset are applied to the item. Unlike other techniques for using polynucleotides as taggants that label an item with only a single polynucleotide sequence, the techniques of this disclosure use multiple polynucleotides with different, random sequences that collectively function as the anti-counterfeit tag. The number of polynucleotides may be at least $10^2$, $10^3$, $10^4$, $10^6$, $10^8$, $10^{10}$, at least $10^{12}$, at least $10^{18}$, or more.

The synthetic polynucleotides may be applied to the item in any number of different ways. The synthetic polynucleotides may be applied to the outside of the item or to packaging containing the item. If the item is liquid or powder, the synthetic polynucleotides may be mixed in with the item. In some implementations, the synthetic polynucleotides may be placed on, in, or under a visible taggant such as a QR code or holographic sticker. The synthetic polynucleotides applied to the item may be protected by a coating or encapsulating layer that can be applied together with the polynucleotides or after the polynucleotides have been applied to the item.

At operation 412, the plurality of synthetic polynucleotides is collected from the item. The synthetic polynucleotides may be collected using any established techniques for collecting polynucleotides from environmental or forensic samples. Following collection, the synthetic polynucleotides may be cleaned or processed in preparation for sequencing using commercial kits or any one of a number of techniques known to those of ordinary skill in the art.

If the item is authentic, then the polynucleotides collected from the item will have the same ratio of nucleoside bases at each position in the random sequences as the polynucleotides synthesized at operation 402. Thus, fewer than all of the polynucleotides applied to the item may be collected and sequenced so long as the polynucleotides that are sequenced have the same ratio of nucleoside bases as the original set of polynucleotides placed on the item. If the item is a counterfeit or a forgery without an anti-counterfeit tag, there will be no polynucleotides to collect from the item. If the anti-counterfeit tag itself is not successfully forged, the polynucleotides collected from the item will have a different ratio of nucleoside bases at some or all of the positions in the sequences and can be detected as such.

At operation 414, at least a portion of the plurality of the synthetic polynucleotides collected from the item are sequenced. The polynucleotides collected from the item may be sequenced using any sequencing technology such as, for example, nanopore sequencing. The method of sequencing used at operation 416 may be the same or different than the method of sequencing used at operation 406.

The portion of the plurality of synthetic polynucleotides that is sequenced may include a large number of polynucleotides such as at least $10^4$ polynucleotides, at least $10^8$ polynucleotides, at least $10^{12}$ polynucleotides, or at least $10^{18}$ polynucleotides. In some implementations, fewer than all of the polynucleotides collected from the item at operation 412 are sequenced. Sequencing fewer than all of the synthetic polynucleotides collected reduces the sequencing cost, and thus, reduces the cost to validate the authenticity of the item. It may be possible to determine the ratio of nucleoside bases with reasonable accuracy from a relatively small subset of the total number of polynucleotides. For example, the size of the portion of synthetic polynucleotides that are sequenced may be no more than 0.1%, 1%, 5%, or 10% of the polynucleotides collected from the item. The size of the portion of the synthetic polynucleotides that are sequenced may be no more than $10^4$, $10^6$, $10^8$, or $10^{10}$ polynucleotides.

The size of the portion of the synthetic polynucleotides collected from the item that is sequenced may be based on the desired level of confidence in the accuracy of the validation. Lower levels of confidence in the accuracy of the validation may be acceptable for lower value items. Thus, the size of the portion of the polynucleotides that is sequenced may be based on a value of the item. The larger portion of the polynucleotides may be sequenced for higher value items and a smaller portion of the polynucleotides may be sequenced for lower value items.

The output generated by sequencing the polynucleotides collected from the item is a plurality of retrieved sequences. The plurality of retrieved sequences represents the order of nucleoside bases in the polynucleotides collected from the item as detected by the sequencing system. The plurality of retrieved sequences may be represented electronically in a computer file.

At operation 416, the plurality of the retrieved sequences are provided to a computing device communicatively connected to the electronic record. In some implementations, a computer file containing the plurality of retrieved sequences may be transmitted over a communications network such as the Internet from a computing device coupled to the sequencer to a network-based computing device that stores or maintains the electronic record. In some implementations, the ratio of nucleoside bases at each position in the retrieved sequences may be calculated locally and only the ratios along with the corresponding positions transmitted over a network to the computing device communicatively connected to the electronic record.

At operation 418, the random sequences in the plurality of retrieved sequences are aligned. The random sequences may be aligned relative to the alignment regions to create alignment of the retrieved sequences. Alternatively, if the synthetic polynucleotides only include random sequences, the random sequences may be aligned to each other without reference to any non-random sequences. Sequences without alignment regions may be aligned by length. In one implementation, all sequences that are not the same length as the synthetic polynucleotides (e.g., shorter or longer due to an error or damage) are not used. The alignment is then created only from those sequences that are the same length as the synthetic polynucleotides. Alignment of the retrieved sequences allows for identification of positions in the sequences and calculation of nucleoside base ratios at each position. Alignment may be performed by a computing device connected to a sequencer that read the sequences of the polynucleotides or by a network-accessible computing device communicatively connected to the electronic record.

At operation 420, a calculated base ratio for positions in the random sequences is calculated from the alignment of the retrieved sequences. The calculated base ratio may be determined by identifying the percentage of total base calls at each position for each of the nucleoside bases. The result will not be a single ratio (i.e., like a % GC content) but a series or string of ratios one for each of the positions in the random sequences. Depending on the length of the random sequence this may be 50, 100, 150, or more ratios. Due to errors in synthesis, damage to the polynucleotides while placed on the item, and errors in sequencing, the ratio of nucleoside bases detected may be different than that used to synthesize the synthetic polynucleotides. For example, at a given position in the synthetic polynucleotides, the original synthesis may be performed with a ratio of 50% A and 50% T. However, the calculated base ratio at the same position from the polynucleotides collected from the item may be 48% A, 1% G, 0% C, 51% T.

Additionally, the polynucleotides sequenced at operation 414 may have a slightly different ratio of nucleoside bases than the entire population of polynucleotides synthesized at operation 402 even if there were no errors or damage to the polypeptides. If the sample sequenced at operation 414 represents only a small portion of the total polynucleotides it may be a non-representative sample that contains different ratios than the entire set of polynucleotides. For example, at a given position in the synthetic polynucleotides, the original synthesis may be performed with a ratio 33.3% A, 33.3% G, and 33.3% C. However, the calculated base ratio at the same position from the polynucleotides collected from the item may be 33.1% A, 33.5% G, 33.3% C, 0% T.

At operation 422, the calculated base ratio is compared to the specific, predetermined ratio of nucleoside bases stored in the electronic record. The item may be determined to be authentic if the two sets of base ratios match. A match is not limited to exact matches. Even for authentic items in which synthetic polynucleotides in the anti-counterfeit tag have not changed, there may be differences in the retrieved sequences obtained from the item as compared to the original sequences placed on the item. The differences may arise from errors in synthesis or in sequencing either initially or at the time of validation. The differences may also arise from damage that occurs to the polynucleotides. Additionally, the subset of polynucleotides sequenced to generate the retrieved sequences may have different base ratios than the original set of polynucleotides. To account for these possible sources of difference, the item may be determined to be authentic if there is at least a threshold level of similarity between the calculated base ratio and the specific, predetermined ratio of nucleoside bases stored in the electronic record.

The base ratios at a specific position in the random sequences may be determined to be a match if the percentage of each nucleotide varies by less than a threshold amount such as, for example, 0.1%, 0.5%, 1%, or 5%. For example, a calculated base ratio of (0.3% A, 49.8% G, 49.9% C, 0% T) may be considered to match within a threshold level of 0.5% similarity the base ratio of (0% A, 50% G, 50% A, 0% T). Partial matches or approximate matches may also be determined based on only a portion of the length of the random sequences. For example, due to sequencing errors or damage particular regions of the polynucleotides such as the ends of the random sequences may have lower accuracy. Thus, comparison of the calculated base ratio and the specific, predetermined ratio of nucleoside bases stored in the electronic record we exclude some portion or percentage of the sequences. For example, a threshold level of similarity may be based on matches between the respective base ratios over some threshold portion of the random sequences such as 80%, 85%, 90%, 95%, or 99%.

If the plurality of synthetic polynucleotides encodes composite letters, comparison of the calculated base ratio to the specific, predetermined ratio of nucleoside bases stored in the electronic record may be implemented by comparing composite letters rather than comparison of the base ratios directly. The calculated base ratio from each position in the retrieved sequences may be converted to a composite letter and determined if the same composite letter is found in that position in the original sequences. Use of composite letters is a way to account for approximate matches and variations in the precise percentages of each nucleoside base.

Converting the calculated base ratio at a position in the retrieved sequences to a composite letter may be thought of as "calling" or identifying which composite letter is most likely encoded by the polynucleotides at that position. Given that there is only a discrete number of possibilities for composite letters, the alphabet of composite letters, the base ratios at each position are evaluated to determine the best match out of all the possible composite letters. This is done by determining that the calculated base ratio is more similar to a one of a plurality of predetermined nucleoside base ratios representing composite letters than to any other of the predetermined nucleoside base ratios.

In some implementations, the ratio of nucleotide bases calculated at operation 420 is converted into a hash. Thus, the ordered string of ratios or percentages is converted into a hash using any conventional technique for creating a hash of data. Similarly, if the ratio of nucleotide bases is converted into a barcode, the barcode may be hashed. Then the comparison may be between the original hash stored in the electronic record and the hash generated from the retrieved sequences. If the two hashes are identical then the base ratios are determined to match. Because the hash in the electronic record cannot be decoded to discover the predetermined ratios of nucleoside bases, even if there is unauthorized access to the electronic record it will not provide useful information to a bad actor.

The comparison may also include a comparison of the structure and patterns of random/non-random sequences in the polynucleotides. For example, the comparison may compare the lengths of the non-random sequences (e.g., alignment region(s) 200) and/or random sequences (e.g., random sequence 202). Comparing the lengths may detect a forged tag that was designed by a bad actor to have the same ratios of nucleoside bases but that does so with polynucleotides that have a different structure than the authentic tag. The comparison may identify if there are any random/non-random sequences positioned relative to each other differently than in the original polynucleotides. For example, if a non-random sequence is present in the middle of a random sequence (e.g., synthetic polynucleotide 212 shown in FIG. 2B) the retrieved sequences can be compared to the original sequences to determine if a non-random sequence also present within the random sequence. These comparisons of sequence length and random/non-random sequence patterns may be done without comparison of specific nucleoside sequences.

The comparison may also include a comparison of a portion of the retrieved sequences to a portion of the original sequences. Comparison of the sequences of random sequences of the polynucleotides may be done to confirm that the polynucleotides found on the item are the same polynucleotides used as the anti-counterfeit tag. As mentioned above, if the specific, predetermined ratios of nucleoside bases are known to a bad actor, the bad actor may be able to create a separate batch of random polynucleotides with the same ratios of nucleoside bases. However, the random polynucleotides created by the bad actor will not have the same sequences as the polynucleotides in the actual anti-counterfeit tag. Therefore, comparing the actual sequences of a portion of the retrieved sequences (e.g., $10^2$, $10^3$, $10^4$, $10^5$, or $10^6$ polynucleotide sequences) to the original sequences can identify if the polynucleotides on the item have different sequences even if they have the same ratios of nucleoside bases. This may be done by determining if a small number of retrieved sequences are the same or similar to any of the large number of original sequences. This comparison may also be done based on a threshold level of similar that is less than 100% similarity such as 99 percent identity, 98 percent identity, 95 percent identity, or another threshold.

The percent of sequence identity of two sequences may be determined by any one of a number of techniques used in bioinformatics or computer science and known to those of ordinary skill in the art. Examples include used in bioinformatics include software such as the BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). The Burrows-Wheeler Alignment tool (BWA) alignment tool may also be used to compare the similarity of sequences (Li H, Durbin R. Fast and accurate short read alignment with Burrows-Wheeler transform. *Bioinformatics.* 2009; 25(14): 17541-1760). Multiple algorithms for string comparison are discussed in D. Gusfield, Algorithms on Strings, Trees, & Sequences, New York, USA: Cambridge University Press, 1997.

The determination of similarity between the two sets of base ratios or composite letters may be made by the computing device that maintains the electronic record. Thus, the comparison may be done by a computing device that is located in the cloud and managed by a third party. The third party may be an entity that is not otherwise associated with the item or the transaction of the item. Alignment and calculation of base ratios from many millions or billions of sequences may be a very computationally intensive operation that is difficult for conventional desktop computers or laptop computers to complete in a reasonable time. Cloud-based computing resources may be used to make such a comparison in a relatively short amount of time such as less than five minutes, less than one minute, less than 30 seconds, or less than 10 seconds.

At operation 424, it is determined if there is at least a threshold level of similarity between the calculated base ratio and the specific, predetermined ratio of nucleoside bases stored in the electronic record or between the corresponding hash values. The determination of a threshold level of similar may be done by any of the techniques discussed above. Thus, in some implementations the comparison of the nucleoside base ratios may be done indirectly such as the comparison of a first barcode hash to a second barcode hash. If at least the threshold level of similarity is found, process 400 proceeds along the "yes" path to operation 426. At operation 426, the computing device that is communicatively connected to the electronic record may generate an indication of authenticity and send that indication to a different computing device. The indication of authenticity may be displayed on the receiving computing device. The indication of authenticity may be an email or other electronic communication. In some implementations, the indication of authenticity may be encrypted. The computing device that receives the indication of authenticity may be a computing device used for sequencing the polynucleotides collected from the item or a different computing device such as another computing device under the control of a purchaser or potential purchaser of the item.

If, however, there is no match between the calculated base ratio and the specific, predetermined ratio of nucleoside bases stored in the electronic record or if the match has less than a threshold level of similarity then the item may be determined to be inauthentic. In which case process 400 proceeds along the "no" path to operation 428.

At operation 428, an indication of inauthenticity is received from the computing device that is communicatively connected to the electronic record. The indication of inauthenticity may be communicated to a receiving computing device that the item could not be authenticated and may be a counterfeit or a forgery. The receiving computing device may display an indication that the item could not be validated as authentic.

Illustrative Computer Architecture

Figure 5:
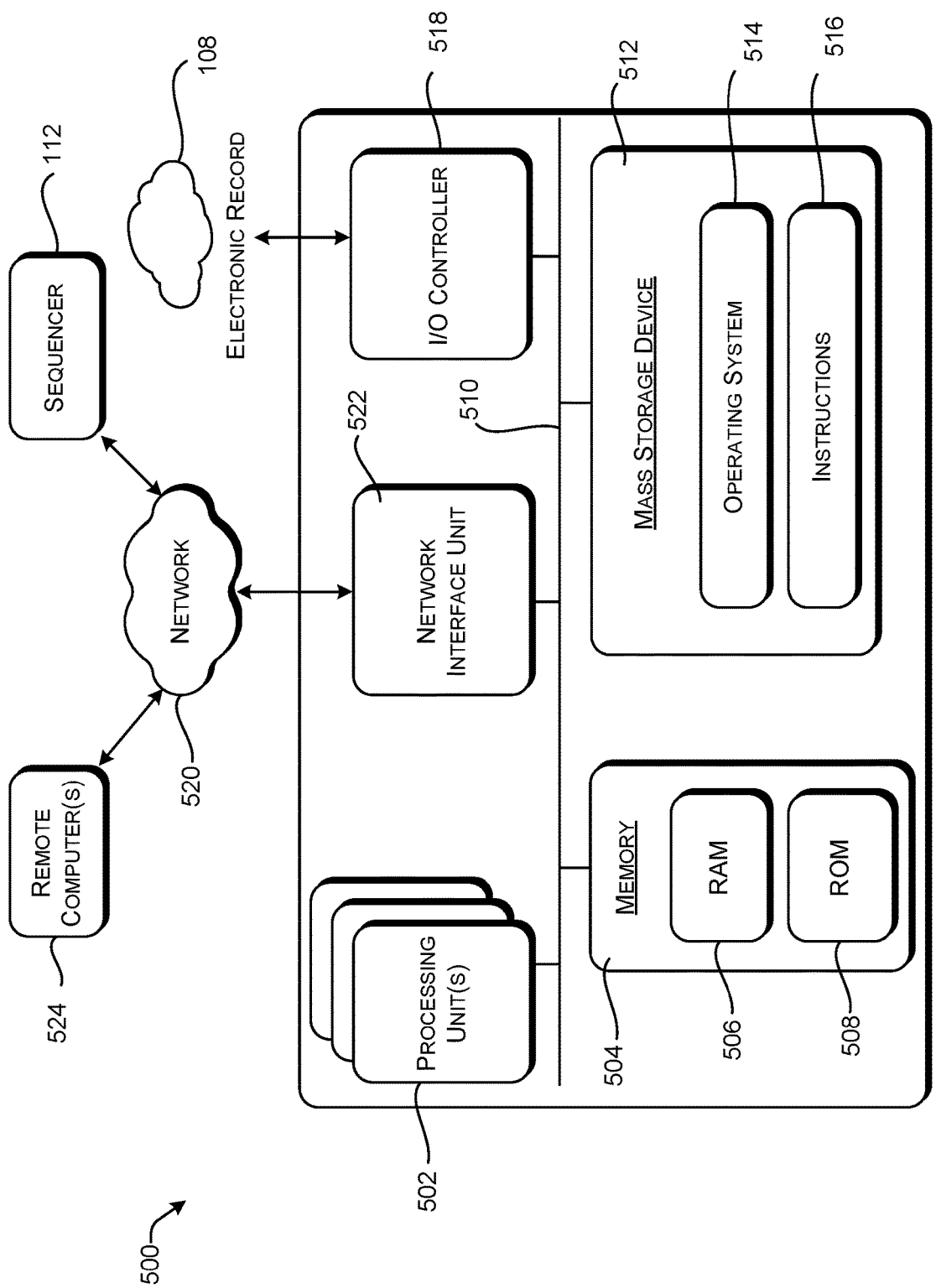
FIG. 5 is an illustrative computer architecture for implementing techniques of this disclosure.

FIG. 5 is a computer architecture diagram showing an illustrative computer hardware and software architecture for a computing device such as the computing device 110 or the computing device 114 introduced FIG. 1. In particular, the computer 500 illustrated in FIG. 5 can be utilized to receive raw data from a sequencer 112 or to maintain the electronic record 108.

The computer 500 includes one or more processing units 502, a system memory 504, including a random-access memory 506 ("RAM") and a read-only memory ("ROM") 508, and a system bus 510 that couples the memory 504 to the processing unit(s) 502. A basic input/output system ("BIOS" or "firmware") containing the basic routines that help to transfer information between elements within the computer 500, such as during startup, can be stored in the ROM 508. The computer 500 further includes a mass storage device 512 for storing an operating system 514 and other instructions 516 that represent application programs and/or other types of programs. The other programs may be, for example, instructions to compare the calculated base ratios to ratios of nucleotide bases 106 and determine if there is at least a threshold level of similarity. The mass storage device 512 can also be configured to store files, documents, and data. In some implementations, electronic record 108 may be maintained in the mass storage device 512.

The mass storage device 512 is connected to the processing unit(s) 502 through a mass storage controller (not shown) connected to the bus 510. The mass storage device 512 and its associated computer-readable media provide non-volatile storage for the computer 500. Although the description of computer-readable media contained herein refers to a mass storage device, such as a hard disk, CD-ROM drive, DVD-ROM drive, or USB storage key, it should be appreciated by those skilled in the art that computer-readable media can be any available computer-readable storage media or communication media that can be accessed by the computer 500.

Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner so as to encode information in the signal. By way of example, and not limitation, communication media includes wired media such as a wired network or direct-wired connection, and wireless media such as acoustic, radio frequency, infrared, and other wireless media. Combinations of any of the above should also be included within the scope of computer-readable media.

By way of example, and not limitation, computer-readable storage media can include volatile and non-volatile, removable and non-removable media implemented in any method or technology for storage of information such as computer-readable instructions, data structures, program modules, or other data. For example, computer-readable storage media includes, but is not limited to, RAM 506, ROM 508, EPROM, EEPROM, flash memory or other solid-state memory technology, CD-ROM, digital versatile disks ("DVD"), HD-DVD, BLU-RAY, 4K Ultra BLU-RAY, or other optical storage, magnetic cassettes, magnetic tape, magnetic disk storage or other magnetic storage devices, or any other medium that can be used to store the desired information and which can be accessed by the computer 500. For purposes of the claims, the phrase "computer-readable storage medium," and variations thereof, does not include waves or signals per se or communication media.

According to various configurations, the computer 500 can operate in a networked environment using logical connections to a remote computer(s) 524 through a network 520. For example, if the computer 500 corresponds to computing device 114 then the remote computer 524 may correspond to the computing device 110. The computer 500 can connect to the network 520 through a network interface unit 522 connected to the bus 510. It should be appreciated that the network interface unit 522 can also be utilized to connect to other types of networks and remote computer systems. The computer 500 can also include an input/output controller 518 for receiving and processing input from a number of other devices, including a keyboard, mouse, touch input, an electronic stylus (not shown), or equipment such as a sequencer 112 for detecting the sequence of polynucleotides. Similarly, the input/output controller 518 can provide output to a display screen or other type of output device (not shown).

It should be appreciated that the software components described herein, when loaded into the processing unit(s) 502 and executed, can transform the processing unit(s) 502 and the overall computer 500 from a general-purpose computing device into a special-purpose computing device customized to facilitate the functionality presented herein. The processing unit(s) 502 can be constructed from any number of transistors or other discrete circuit elements, which can individually or collectively assume any number of states. More specifically, the processing unit(s) 502 can operate as a finite-state machine, in response to executable instructions contained within the software modules disclosed herein. These computer-executable instructions can transform the processing unit(s) 502 by specifying how the processing unit(s) 502 transitions between states, thereby transforming the transistors or other discrete hardware elements constituting the processing unit(s) 502.

Encoding software modules can also transform the physical structure of the computer-readable media presented herein. The specific transformation of physical structure depends on various factors, in different implementations of this description. Examples of such factors include, but are not limited to, the technology used to implement the computer-readable media, whether the computer-readable media is characterized as primary or secondary storage, and the like. For example, if the computer-readable media is implemented as semiconductor-based memory, the software disclosed herein can be encoded on the computer-readable media by transforming the physical state of the semiconductor memory. For instance, the software can transform the state of transistors, capacitors, or other discrete circuit elements constituting the semiconductor memory. The software can also transform the physical state of such components to store data thereupon.

As another example, the computer-readable media disclosed herein can be implemented using magnetic or optical technology. In such implementations, the software presented herein can transform the physical state of magnetic or optical media, when the software is encoded therein. These transformations can include altering the magnetic characteristics of particular locations within given magnetic media. These transformations can also include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer 500 to store and execute software components and functionalities presented herein. It also should be appreciated that the architecture shown in FIG. 5 for the computer 500, or a similar architecture, can be utilized to implement many types of computing devices such as desktop computers, notebook computers, servers, supercomputers, gaming devices, tablet computers, and other types of computing devices known to those skilled in the art. It is also contemplated that the computer 500 might not include all of the components shown in FIG. 5, can include other components that are not explicitly shown in FIG. 5, or can utilize an architecture completely different than that shown in FIG. 5.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method of tagging an item (102) with an anti-counterfeit tag (100), the method comprising: synthesizing a plurality of synthetic polynucleotides (104) comprising random sequences (202) with a specific, predetermined ratio of nucleoside bases at each position in the random sequences, wherein the specific, predetermined ratio of nucleoside bases varies across the positions of the random sequences; registering, in an electronic record (108) the specific, predetermined ratio of nucleoside bases and a description of the item; and applying at least a portion of the plurality of synthetic polynucleotides to the item.

Clause 2. The method of clause 1, wherein synthesizing the plurality of synthetic polynucleotides comprises phosphoramidite synthesis with a ratio of individual nucleoside bases that is varied over individual rounds of nucleoside phosphoramidite addition.

Clause 3. The method of clause 1, wherein synthesizing the plurality of synthetic polynucleotides comprises enzymatic single-base-addition synthesis with a ratio of individual nucleoside bases that is varied over individual rounds of nucleoside triphosphate addition.

Clause 4. The method of any of clauses 1-3, wherein the plurality of synthetic polynucleotides further comprises alignment regions (200) that are non-random and share a same position in each of the plurality of synthetic polynucleotides relative to the random sequences.

Clause 5. The method of clause 4, wherein a sequence of the alignment regions is the same for all of the plurality of synthetic polynucleotides Clause 6. The method of any of clauses 1-5, wherein the specific, predetermined ratio of nucleoside bases at each position in the random sequences is one of several predetermined ratios representing composite letters (314) that each vary from each other by at least a 25% difference in an amount of one of the nucleoside bases.

Clause 7. The method of any of clauses 1-6, wherein the specific, predetermined ratio of nucleoside bases at each position in the random sequences is a ratio of two or more nucleoside bases.

Clause 8. The method of any of clauses 1-7, further comprising sequencing at least a portion of the plurality of synthetic polynucleotides to obtain a plurality of original sequences (106).

Clause 9. The method of any of clauses 1-8, further comprising taking a random subset of the plurality of synthetic polynucleotides prior to applying the synthetic polynucleotides to the item.

Clause 10. The method of clause 9, wherein applying at least a portion of the plurality of synthetic polynucleotides to the item comprises applying the random subset of the plurality of synthetic polynucleotides to the item.

Clause 11. The method of any of clauses 1-10, further comprising: determining a barcode (304), wherein the specific, predetermined ratio of nucleoside bases used for synthesizing the plurality of synthetic polynucleotides at each position in the random sequences encodes the barcode using composite letters.

Clause 12. A method of authenticating an item with an anti-counterfeit tag (100), the method comprising: collecting a plurality of synthetic polynucleotides (104) from the item (102), wherein the plurality of synthetic polynucleotides comprise random sequences with a specific, predetermined ratio of nucleoside bases at each position in the random sequences, wherein the specific, predetermined ratio of nucleoside bases varies across the positions of the random sequences; sequencing a portion of the plurality of synthetic polynucleotides collected from the item to obtain a plurality of retrieved sequences; aligning the random sequences in the plurality of retrieved sequences to create an alignment of the retrieved sequences; calculating, from the alignment of the retrieved sequences, a calculated base ratio of nucleoside bases at positions in the random sequences; and determining that the item is authentic based on comparison of the calculated base ratio to the specific, predetermined ratio of nucleoside bases stored in an electronic record (108).

Clause 13. The method of clause 12, wherein a size of the portion of the plurality of synthetic polynucleotides that is sequenced is no more than 10% of the plurality of synthetic polynucleotides collected from the item.

Clause 14. The method of clause 12 or 13, wherein the plurality of synthetic polynucleotides further comprises alignment regions that are not random and share a same position in each of the plurality of synthetic polynucleotides relative to the random sequences, and wherein aligning the random sequences is performed relative to the alignment regions.

Clause 15. The method of any of clauses 12-14, wherein determining that the item is authentic based on comparison of the calculated base ratio to the specific, predetermined ratio of nucleoside bases stored in the electronic record comprises: determining, for each position in the random sequences, that the calculated base ratio is more similar to a one of a plurality of predetermined nucleoside base ratios representing a composite letter (314) than to any other of the predetermined nucleoside base ratios and comparing the composite letters determined from the calculated base ratio to composite letters encoded by the plurality of synthetic polynucleotides.

Clause 16. The method of clause 15, wherein the composite letters encode a barcode and comparison of the calculated base ratio to the specific, predetermined ratio of nucleoside bases stored in the electronic record comprises comparison of a barcode encoded by the calculated base ratio to a barcode stored in the electronic record.

Clause 17. The method of any of clauses 12-16, wherein determining that the item is authentic based on comparison of the calculated base ratio to the specific, predetermined ratio of nucleoside bases stored in the electronic record comprises: determining that there is at least a threshold level of similarity between the calculated base ratio and the specific, predetermined ratio of nucleoside bases stored in the electronic record.

Clause 18. The method of any of clauses 12-17, further comprising: providing the plurality of retrieved sequences to a computing device (110) communicatively connected to the electronic record; and receiving from the computing device (110) storing the electronic record an indication of authenticity (118), wherein calculating the calculated base ratio is performed by the computing device (110) communicatively connected to the electronic record (108).

Clause 19. The method of any of clauses 12-18, wherein determining that the item is authentic further comprises a comparison of the structure and patterns of random/non-random sequences in the polynucleotides.

Clause 20. The method of any of clauses 12-19, wherein determining that the item is authentic further comprises a comparison of a portion of the retrieved sequences to a portion of the original sequences.

Clause 21. An item (102) labeled with an anti-counterfeit tag (100), wherein the anti-counterfeit tag is a plurality of synthetic polynucleotides (104) comprising: random sequences (202) with a specific, predetermined ratio of nucleoside bases at each position (204) in the random sequences, wherein the specific, predetermined ratio of nucleoside bases varies across the positions of the random sequences, wherein the specific, predetermined ratio of nucleoside bases is uniquely associated in an electronic record (108) with the item thereby indicating authenticity of the item.

Clause 22. The item of clause 21, wherein the synthetic polynucleotides further comprise alignment regions that are not random and share a same position in each of the plurality of synthetic polynucleotides relative to the random sequences.

Clause 23. The item of clause 20 or 21, wherein the plurality of synthetic polynucleotides is synthesized by column synthesis and a number of the plurality of synthetic polynucleotides with unique random sequences is at least $10^{12}$ polynucleotides.

Conclusion

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

For ease of understanding, the processes discussed in this disclosure are delineated as separate operations represented as independent blocks. However, these separately delineated operations should not be construed as necessarily order-dependent in their performance. The order in which the processes are described is not intended to be construed as a limitation, and unless other otherwise contradicted by context any number of the described process blocks may be combined in any order to implement the process or an alternate process. Moreover, it is also possible that one or more of the provided operations is modified or omitted.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications throughout this specification. Each of the cited references is individually incorporated herein by reference for its particular cited teachings as well as for all that it discloses.

The invention claimed is:

1. A method of tagging an item with an anti-counterfeit tag, the method comprising:
   synthesizing a plurality of synthetic polynucleotides comprising random sequences with a specific, predetermined ratio of nucleoside bases at each position in the random sequences, wherein the specific, predetermined ratio of nucleoside bases varies across the positions of the random sequences;
   registering, in an electronic record the specific, predetermined ratio of nucleoside bases and a description of the item;
   determining, a threshold level of similarity to be used when comparing each position of the predetermined ratio of nucleoside bases in the electronic record with each position of a calculated base ratio from a retrieved sequence; and
   applying at least a portion of the plurality of synthetic polynucleotides to the item.

2. The method of claim 1, wherein synthesizing the plurality of synthetic polynucleotides comprises phosphoramidite synthesis with a ratio of individual nucleoside bases that is varied over individual rounds of nucleoside phosphoramidite addition.

3. The method of claim 1, wherein synthesizing the plurality of synthetic polynucleotides comprises enzymatic single-base-addition synthesis with a ratio of individual nucleoside bases that is varied over individual rounds of nucleoside triphosphate addition.

4. The method of claim 1, wherein the plurality of synthetic polynucleotides further comprises alignment regions that are non-random and share a same position in each of the plurality of synthetic polynucleotides relative to the random sequences.

5. The method of claim 1, wherein the specific, predetermined ratio of nucleoside bases at each position in the random sequences is one of several predetermined ratios representing composite letters that each vary from each other by at least a 25% difference in an amount of one of the nucleoside bases.

6. The method of claim 1, wherein the specific, predetermined ratio of nucleoside bases at each position in the random sequences is a ratio of two or more nucleoside bases.

7. The method of claim 1, further comprising sequencing at least a portion of the plurality of synthetic polynucleotides to obtain a plurality of original sequences.

8. The method of claim 1, further comprising taking a random subset of the plurality of synthetic polynucleotides prior to applying the synthetic polynucleotides to the item.

9. The method of claim 8, wherein applying at least a portion of the plurality of synthetic polynucleotides to the item comprises applying the random subset of the plurality of synthetic polynucleotides to the item.

10. The method of claim 1, further comprising:
determining a barcode,
wherein the specific, predetermined ratio of nucleoside bases used for synthesizing the plurality of synthetic polynucleotides at each position in the random sequences encodes the barcode using composite letters.

11. A method of authenticating an item with an anti-counterfeit tag, the method comprising:
collecting a plurality of synthetic polynucleotides from the item, wherein the plurality of synthetic polynucleotides comprise random sequences with a specific, predetermined ratio of nucleoside bases at each position in the random sequences, wherein the specific, predetermined ratio of nucleoside bases varies across the positions of the random sequences;
sequencing a portion of the plurality of synthetic polynucleotides collected from the item to obtain a plurality of retrieved sequences;
aligning the random sequences in the plurality of retrieved sequences to create an alignment of the retrieved sequences;
calculating, from the alignment of the retrieved sequences, a calculated base ratio of nucleoside bases at each position in the random sequences; and
determining that the item is authentic based on a threshold level of similarity between a stored predetermined ratio of nucleoside bases for each position in an electronic record with the calculated base ratio for each position from the retrieved sequences.

12. The method of claim 11, wherein a size of the portion of the plurality of synthetic polynucleotides that is sequenced is no more than 10% of the plurality of synthetic polynucleotides collected from the item.

13. The method of claim 11, wherein the plurality of synthetic polynucleotides further comprises alignment regions that are not random and share a same position in each of the plurality of synthetic polynucleotides relative to the random sequences, and
wherein aligning the random sequences is performed relative to the alignment regions.

14. The method of claim 11, wherein determining that the item is authentic based on comparison of the calculated base ratio to the specific, predetermined ratio of nucleoside bases stored in the electronic record comprises:
determining, for each position in the random sequences, that the calculated base ratio is more similar to a one of a plurality of predetermined nucleoside base ratios representing a composite letter than to any other of the predetermined nucleoside base ratios and comparing the composite letters determined from the calculated base ratio to composite letters encoded by the plurality of synthetic polynucleotides.

15. The method of claim 14, wherein the composite letters encode a barcode and comparison of the calculated base ratio to the specific, predetermined ratio of nucleoside bases stored in the electronic record comprises comparison of a barcode encoded by the calculated base ratio to a barcode stored in the electronic record.

16. The method of claim 11, further comprising:
providing the plurality of retrieved sequences to a computing device communicatively connected to the electronic record; and
receiving from the computing device storing the electronic record an indication of authenticity, wherein calculating the calculated base ratio is performed by the computing device communicatively connected to the electronic record.

17. The method of claim 1, wherein the threshold level of similarity is based on a type of protection for the synthetic polynucleotides, a length of time since the item was tagged with the synthetic polynucleotides, a sequencing technique, or a value of the item.

* * * * *